(12) United States Patent
Suh et al.

(10) Patent No.: US 6,593,363 B1
(45) Date of Patent: Jul. 15, 2003

(54) DITERPENE DERIVATIVES AND ANTI-INFLAMMATORY ANALGESIC AGENTS COMPRISING THE SAME

(75) Inventors: Young Ger Suh, 1223-602, Mokryun Apt., Sanbon-dong, Gunpo, Kyungki-do 435-040 (KR); Young Hoon Choi, Seoul (KR); Hye Kyung Lee, Kwacheon (KR); Young Ho Kim, Taejon (KR); Hyoung Sup Park, Seoul (KR)

(73) Assignees: Sae Han Pharm. Co., Ltd., Kyungki-do (KR); Young Ger Suh, Kyungki-do (KR)

( * ) Notice: Subject to any disclaimer, the term of this patent is extended or adjusted under 35 U.S.C. 154(b) by 0 days.

(21) Appl. No.: 09/600,774

(22) PCT Filed: Jan. 25, 1999

(86) PCT No.: PCT/KR99/00038

§ 371 (c)(1),
(2), (4) Date: Sep. 15, 2000

(87) PCT Pub. No.: WO99/37600

PCT Pub. Date: Jul. 29, 1999

(30) Foreign Application Priority Data

Jan. 26, 1998 (KR) .......................................... 1998/2441

(51) Int. Cl.$^7$ .......................... C07C 63/44; A61K 31/19
(52) U.S. Cl. ..................... 514/510; 514/557; 548/247; 560/117; 562/499; 568/665; 568/817; 585/21
(58) Field of Search .......................... 560/117; 562/499; 568/665, 817; 585/21; 514/510, 557; 548/247

(56) References Cited

U.S. PATENT DOCUMENTS 6,365,768 B1 * 4/2002 Palladino .................... 560/117

FOREIGN PATENT DOCUMENTS

WO     WO 95/34300     12/1995

OTHER PUBLICATIONS

Kim J. of Natural Products 51 (6) 1080–3 1988.*

Stedman's Medical Dictionary 27$^{th}$ ed. "rheumatism" 2000.*

Cruz et al.; "Relative Sterochemistry Determination of Pimaradienes Through Oxidation Products", Chemical Abstracts, vol. 127: 5208z, p. 594 (1997).

Chamy et al.; "Diterpenoids From Caleolaria Species. Part 10. Dieterpenes From Calceolaria Polifolia", Plant Biochem., vol. 116: 102659c, p. 411 (1992).

Chamy et al.; "Diterpenoids From Caleolaria Species. Part 5. Diterpenes from Calceolaria Lepida", Chemical Abstracts, vol. 114: 20960p, p. 408 (1991).

Morozkov et al.; "Neutral Fraction of the Oleoresin of Pinus Sylvestris. 3 Norditerpene Compounds", Plant Biochem., vol. 77: 98751h, p. 193 (1972).

Suh et al.; "Steroselective Construction of C–13 Quaternary Carbon Unit of Isopimarane Diterpene and its Synthetic Application to Isopimarol Diterpene", Synthetic Communications, 27(4), pp. 587–593, (1997).

* cited by examiner

*Primary Examiner*—Robert Gerstl
(74) *Attorney, Agent, or Firm*—Finnegan, Henderson, Farabow, Garrett & Dunner LLP

(57) ABSTRACT

The present invention relates to diterpene derivatives prepared from the components which are extracted from Acanthopanax Koreanum and represented by Chemical Formula (1).

7 Claims, No Drawings

DITERPENE DERIVATIVES AND ANTI-INFLAMMATORY ANALGESIC AGENTS COMPRISING THE SAME

TECHNICAL FIELD

The present invention relates to diterpene derivatives and anti-inflammatory analgesic agents comprising the same. More specifically, the present invention relates to diterpene derivatives prepared from the components which are extracted from Acanthopanax Koreanum and represented by Chemical Formula 1:

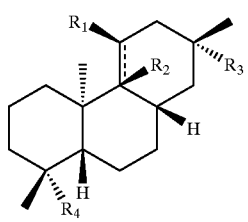

wherein, $R_1$ and $R_2$ individually represent hydrogen or hydroxy, or they form a double bond in the cycle, $R_3$ represents vinyl, hydroxyethyl, methoxyethyl, acetyloxyethyl, methoxymethoxyethyl, methoxyethoxymethoxyethyl, methoxyiminoethyl or isoxazolinyl group, $R_4$ represents hydroxymethyl, carboxyl, carboxymethyl, carboxyvinyl, carboxyethyl, carboxypropyl, carboxybutyl, carboxybutadienyl, carboxyallyl, carboxyhomoallyl, carbamoyl, methylcarbamoyl, hydroxycarbamoyl, carbazoyl, N-pipsylcarbamoylmethyl, N-pipsylcarbamoylethyl, N-pipsylcarbamoylbutadienyl or N-methanesulfonylcarbamoylethyl group; and anti-inflammatory analgesic agents comprising the same.

BACKGROUND ART

Acanthopanax Koreanum is a special product which grows spontaneously in Cheju-do in the Republic of Korea. It is a deciduous shrub belong to the family of Japanese angelica tree, and taking-out of the tree from Cheju-do is restricted. The bark of the tree and the bark of the root have been known to have effective analgesic action on pain of bones and sinews from ancient times in the field of Chinese medicines. Among the people, wine was made from the bark or root-bark of Acanthopanax Koreanum, and the win has been used for treatment of neuralgia, paralysis, hypertension and rheumatism.

Recently, the present inventors found the fact that (−)-pimara-9(11),15-diene-4-carboxylic acid among the diterpene components extracted from root-bark and bark of Acanthopanax Koreanum, and novel derivatives synthesized therefrom inhibits the stage where arachidonic acid is converted to $PGE_2$, an inflammation mediator, thereby having excellent anti-inflammatory action, and the discovery was filed as a patent application (Korean Patent No. 112194).

DISCLOSURE OF THE INVENTION

The present inventors have continuously performed intensive studies in order to discover an excellent inhibitor against production of $PGE_2$(prostagladin $E_2$), and as a result, could additionally develop a compound having more excellent anti-inflammatory action, and complete the present invention.

The object of the present invention is to provide diterpene derivatives represented by Chemical Formula 1.

Another object of the present invention is to provide an anti-inflammatory analgesic agent comprising the diterpene derivative represented by Chemical Formula 1.

The present invention relates to diterpene derivatives represented by Chemical Formula 1 and anti-inflammatory analgesic agents comprising the same.

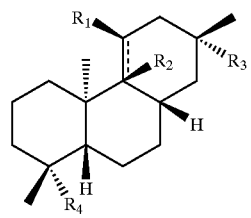

wherein, $R_1$, $R_2$, $R_3$ and $R_4$ are the same as defined previously.

The compound of Chemical Formula 1 is prepared from the components extracted from Acanthopanax Koreanum, and the process for preparation is described in detail herein-below:

First, root-bark and bark of Acanthopanax Koreanum is cut into pieces and the pieces are heat-extracted with alcohol in a water bath, and the extract is filtered. After concentrating the combined filtrate of the alcohol extract, water is added, and the mixture is extracted with diethyl ether. The ether extract is concentrated to dryness, and the residue is fractioned by silica gel column chromatography using a mixture of ethyl acetate and hexane as an eluent, to give (−)-pimara-9(11),15-diene-4-carboxylic acid ($R_4$=COOH) of Chemical Formula 2, the main component of the fractions. In the description of compounds of Chemical Formulas 2 to 48 below, the definitions of $R_1$ to $R_4$ in the parentheses are described in order to show how the substituents $R_1$ to $R_4$ of Chemical Formulas 2 to 48 are characteristically altered as compared to Chemical Formula 1.

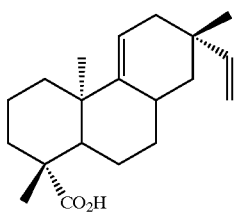

The compound of Chemical Formula 2 is subjected to chemical reactions shown in Reaction Schemes 1 to 7, to form various derivatives.

Scheme 1

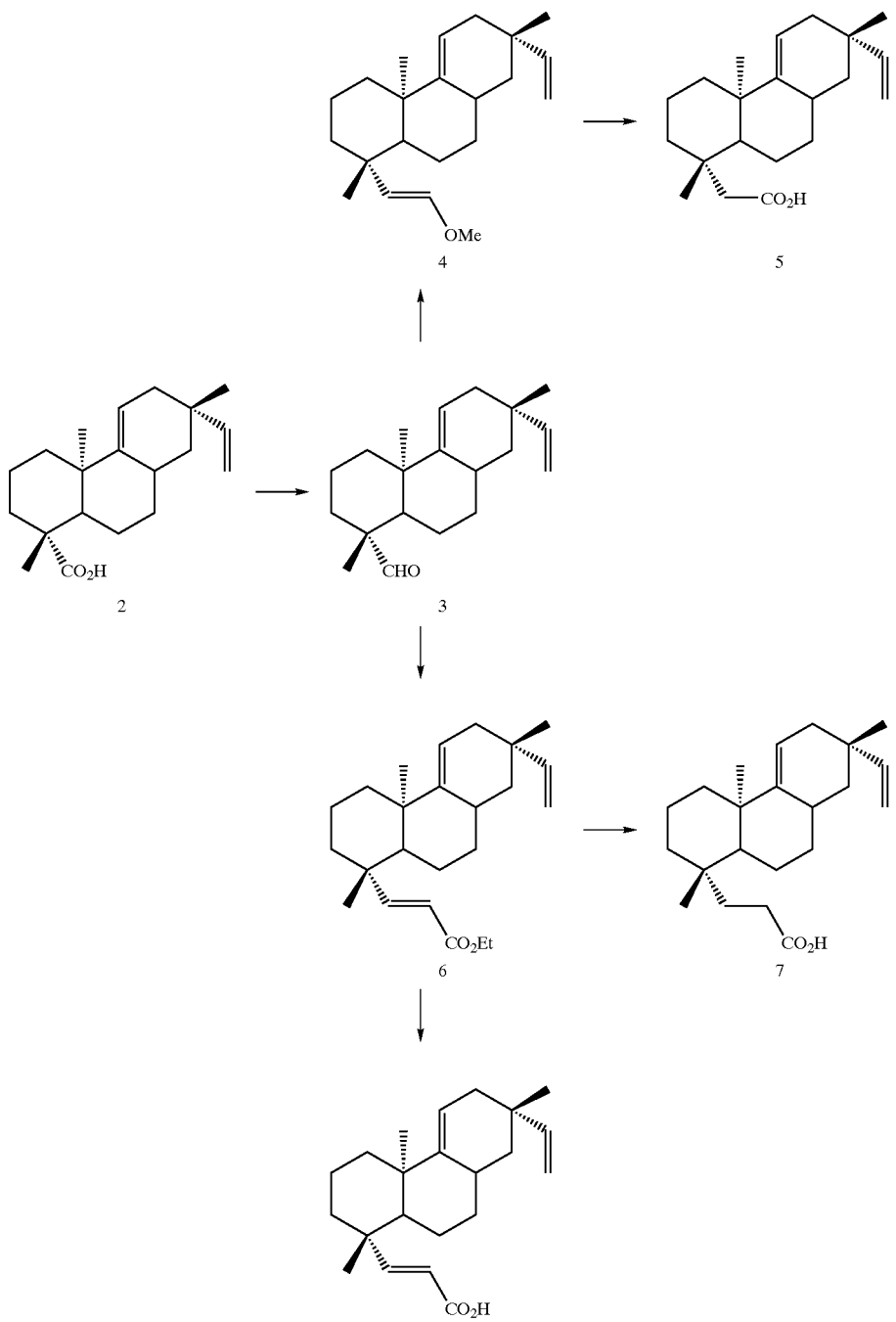

As shown in Reaction Scheme 1, the natural diterpene ($R_4$=COOH) of Chemical Formula 2 is reduced, and then oxidized, using tetrapropylammonium perruthenate, PDC, PCC or Swern oxidation to give a compound ($R_4$=CHO) of Chemical Formula 3. The aldehyde group of the compound of Chemical Formula 3 thus obtained is subjected to Wittig reaction using triethylphosphono acetate anion in tetrahydrofuran to obtain a double bond in the compound of Chemical Formula 6. The double bond of the conjugated ester is reduced by magnesium in methanol, or directly hydrolyzed with lithium hydroxide to obtain a compound of Chemical Formula 7 ($R_4$=$CH_2CH_2$COOH) or that of Chemical Formula 8 ($R_4$=CHCHCOOH). The compound of Chemical Formula 4 ($R_4$=CHCHOCH$_3$) obtained from Wittig reaction using methoxymethyl phosphorane is hydrolyzed by p-toluenesulfonic acid in acetone to give an aldehyde, which is oxidized by silver oxide in water and ethanol to give a compound of Chemical Formula 5 ($R_4$= $CH_2$COOH).

Carbonyl derivatives of the present invention can be prepared according to Reaction Scheme 2 or 3 shown below.

Scheme 2

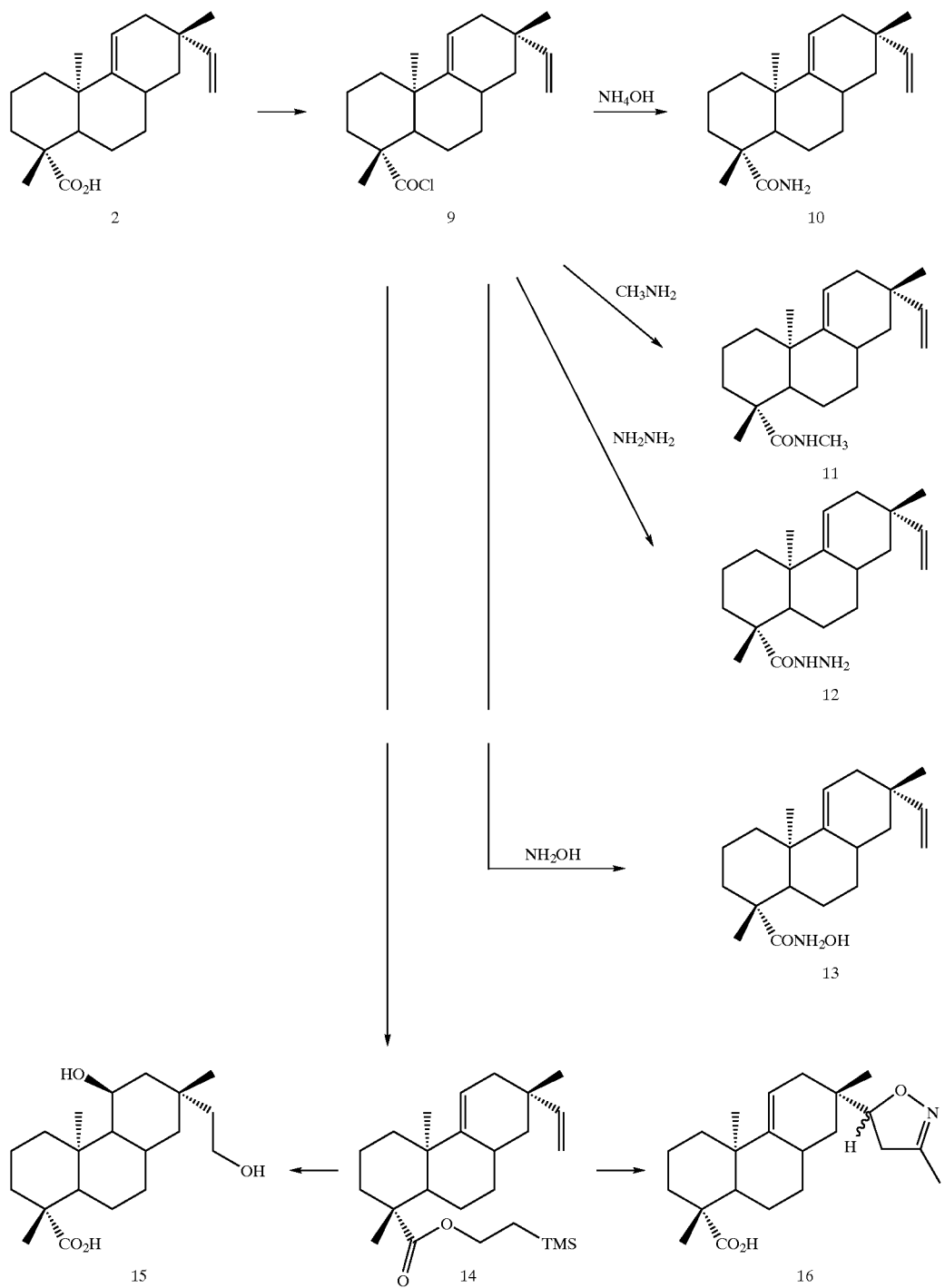

As shown in Reaction Scheme 2, the natural diterpene of Chemical Formula 2 ($R_4$=COOH) is directly reacted with oxalyl chloride or thionyl chloride in benzene to give a compound of Chemical Formula 9 ($R_4$=COCl), which is reacted with aqueous ammonia or aqueous solution of methyl amine in ethyl acetate, with hydroxylamine hydrochloride in benzene, or with hdyrazine monohydrate in dry ether, to give a compound of Chemical Formula 10 ($R_4$=CONH$_2$), a compound of Chemical Formula 11 ($R_4$=CONHCH$_3$), a compound of Chemical Formula 12($R_4$=CONHNH$_2$, carbazoyl), and a compound of Chemical Formula 13 ($R_4$=CONHOH), respectively.

Similarly, the acid chloride group of the compound of Chemical Formula 9 is reacted with trimethylsilyl ethanol in pyridine to give a compound of Chemical Formula 14 ($R_4$=COOCH$_2$CH$_2$TMS) wherein the carboxylic group is protected, which is then reacted with two equivalents of borane-methyl sulfide in tetrahydrofuran and deprotected with tetrabutylammonium fluoride in dimethylformamide to give a compound of Chemical Formula 15 ($R_1$=OH, $R_2$=H, $R_3$=CH$_2$CH$_2$OH, $R_4$=CO$_2$H). Otherwise, the compound of Chemical Formula 14 wherein the carboxylic group is protected ($R_4$=COOCH$_2$CH$_2$TMS) is subjected to additional cyclization using nitrile oxide, which was obtained from N-chlorosuccinimide and acetaldoxime, in tetrahydrofuran, and then deprotected with tetrabutylammonium fluoride to give a compound of Chemical Formula 16 ($R_1$, $R_2$=double bond, $R_4$=isoxazolinyl).

Scheme 3

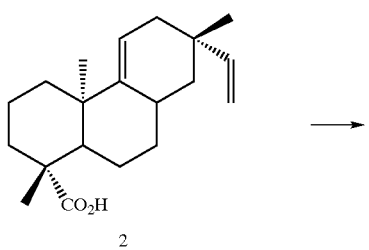

2

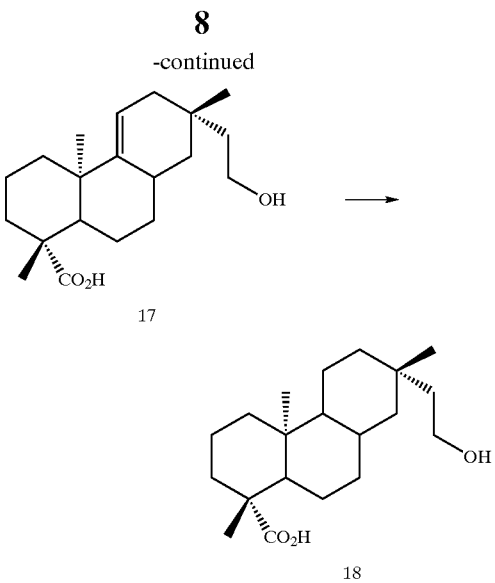

17

18

As shown in Reaction Scheme 3 above, the natural diterpene of Chemical Formula 2 ($R_4$=COOH) is reacted with n-butyllithium in tetrahydrofuran to obtain a carboxylate salt, which is reduced by one equivalent of borane-methyl sulfide complex (BH$_3$—SMe$_2$) to give an objective compound of Chemical Formula 17 ($R_3$=CH$_2$CH$_2$OH), without giving any effect on the carboxylic group. The compound of Chemical Formula 17 thus obtained is reduced on contact to give a compound of Chemical Formula 18 ($R_1$=H$_2$, $R_2$H, $R_3$=CH$_2$CH$_2$OH).

Scheme 4

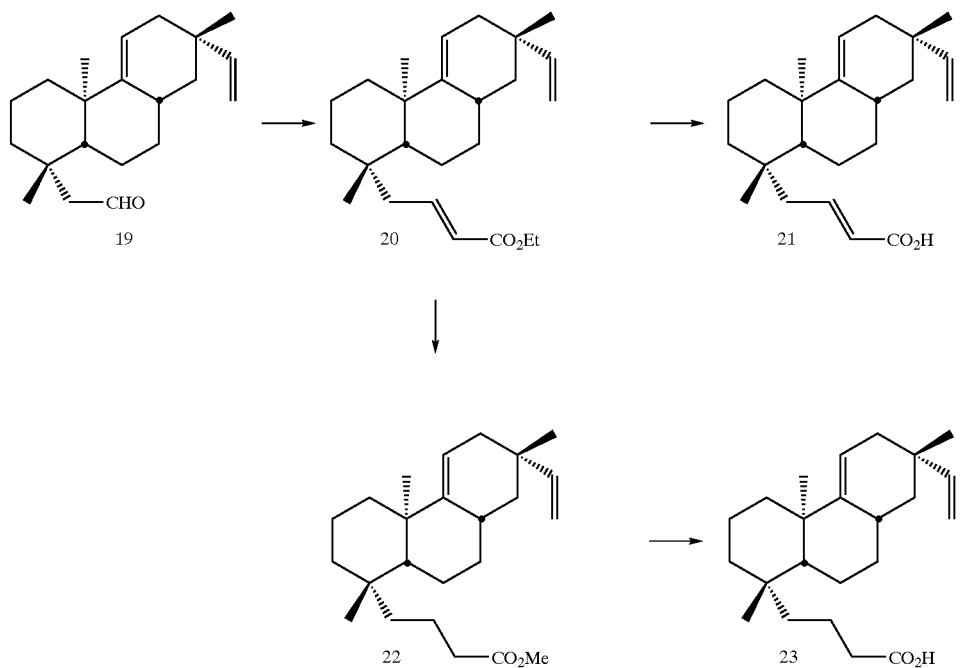

As shown in Reaction Scheme 4 above, the aldehyde group of the compound of Chemical Formula 19 (R$_4$=CH$_2$CHO), which was obtained by hydrolzying the compound of Chemical Formula 4 as in Reaction Scheme 1, is subjected to Wittig reaction in toluene to obtain a double bond. The conjugated ester is directly hydrolyzed by lithium hydroxide, or reduced by magnesium in methanol and hydrolyzed, to provide a compound of Chemical formula 21 (R$_4$=CH$_2$CHCHCOOH) or a compound of Chemical Formula 23 (R$_4$=CH$_2$CH$_2$CH$_2$COOH).

Otherwise, the conjugated ester group of the compound of Chemical Formula 6 (R$_4$=CHCHCO$_2$Et) is reacted with magnesium in methanol to reduce the double bond and with diisobutylaluminium hydride to reduce the ester group, and then oxidized with tetrapropylammonium perruthenate to give a compound of Chemical formula 27 (R$_4$=CH$_2$CH$_2$CHO).

The aldehyde group of the compound of Chemical Formula 27 thus obtained is subjected to Wittig reaction using triethyl phosphonoacetate anion in tetrahydrofuran to obtain

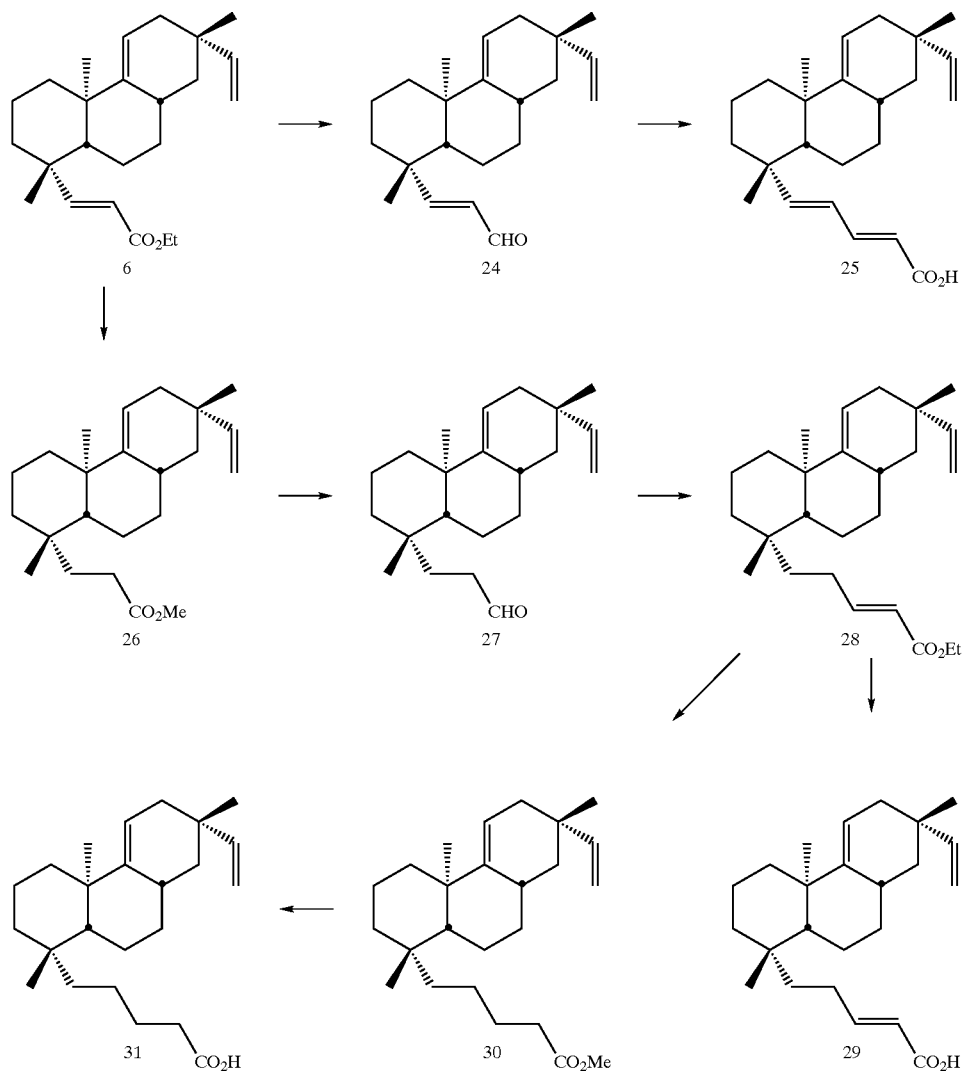

Scheme 5

As shown in Reaction Scheme 5 above, the conjugated ester group of the compound of Chemical Formula 6 (R$_4$=CHCHCO$_2$Et), which was obtained in Reaction Scheme 2, is reduced and then oxidized with tetrapropylammonium perruthenate to provide a compound of Chemical Formula 24 (R$_4$=CHCHCHO). The aldehyde is subjected to Wittig reaction with triethyl phosphonoacetate anion in tetrahydrofuran to give a diene, which is hydrolyzed with lithium hydroxide to provide a compound of Chemical Formula 25(R$_4$=CHCHCHCHCO$_2$H).

a double bond, and the double bond of the conjugated ester is directly hydrolyzed with lithium hydroxide, or reduced with magnesium in methanol and hydrolyzed to provide a compound of Chemical Formula 29 (R$_4$=CH$_2$CH$_2$CHCHCOOH, carboxyhomoallyl) or a compound of Chemical Formula 31 (R$_4$=CH$_2$CH$_2$CH$_2$CH$_2$COOH).

The pipsylcarbamoyl derivatives of the present invention can be prepared as shown in Reaction Scheme 6 below Scheme 6

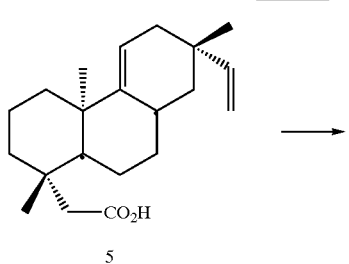
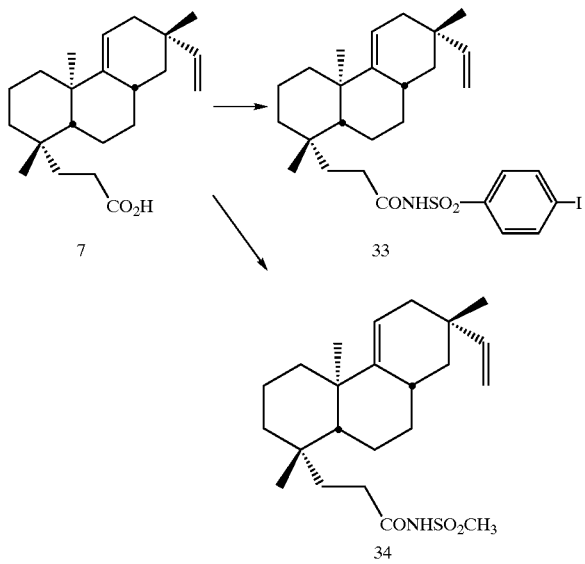
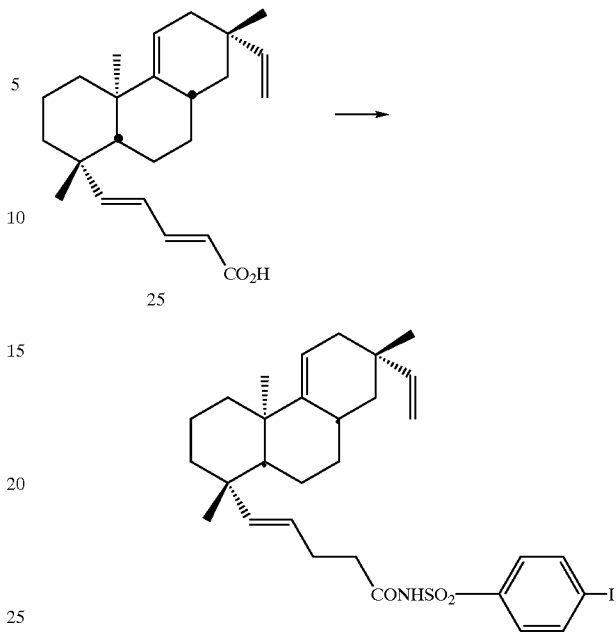

The carboxylic group of the compound of Chemical Formula 5, 7 or 25 is directly reacted with oxalyl chloride or thionyl chloride in benzene, to give an acid chloride, which is then reacted with pipsylamide anion or methanesulfonamide anion obtained by treating pipsylamide or methansulfonamide with sodium hydride in tetrahydrofuran, to give a compound of Chemical Formula 32 ($R_4$=$CH_2CONHSO_2PhI$, pipsylcarbamoylmethyl), a compound of Chemical Formula 33 ($R_4$=$CH_2CH_2CONHSO_2PhI$, pipsylcarbamoylethyl), a compound of Chemical Formula 34 ($R_4$=$CH_2CH_2CONHSO_2CH_3$, methanesulfonylcarbamoylethyl) and a compound of Chemical Formula 35 ($R_4$=$CHCHCHCHCONHSO_2PhI$, pipsylcarbamoylbutadienyl), respectively.

Scheme 7

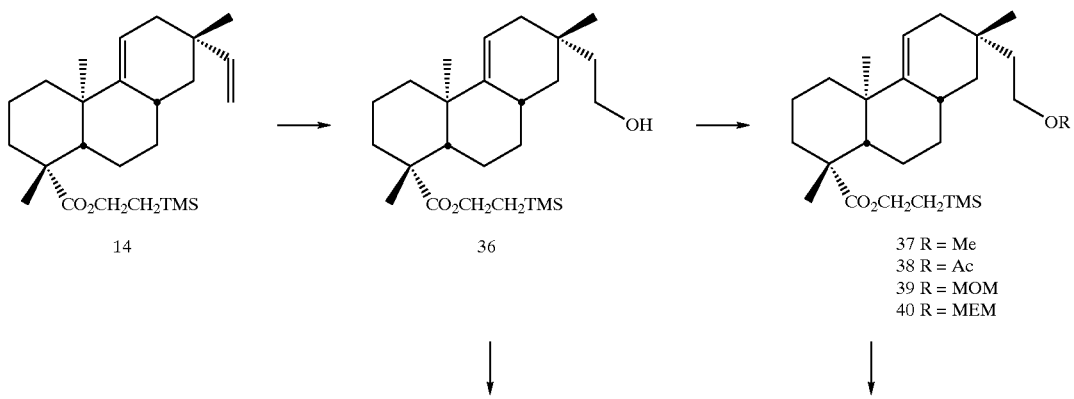

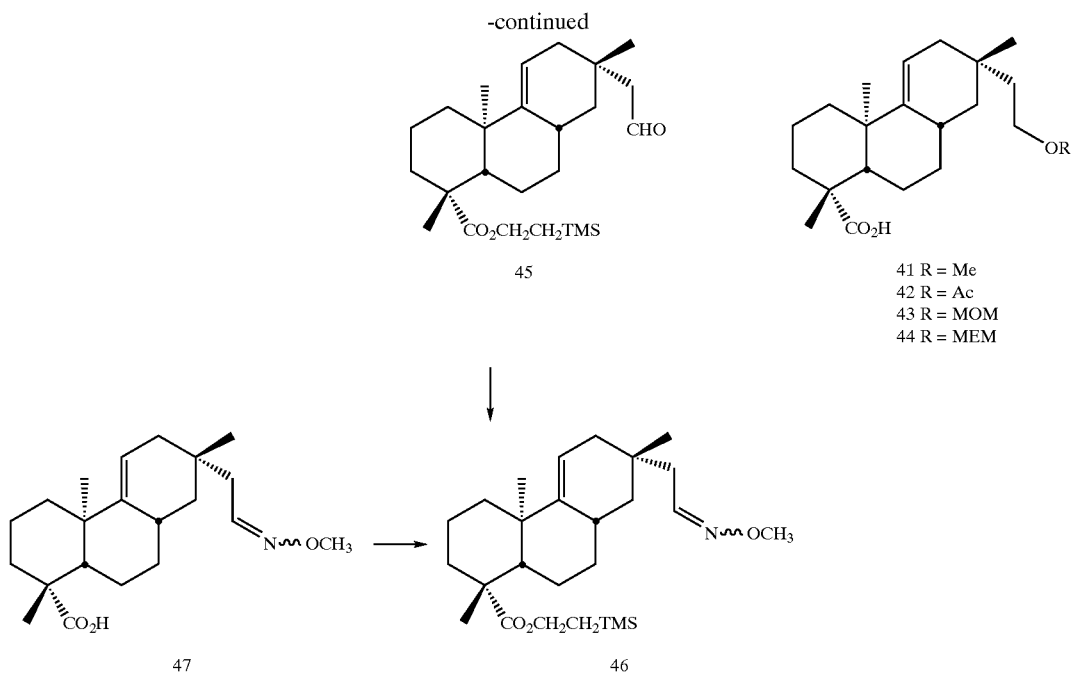

As shown in Reaction Scheme 7 above, the hydroxy group of the compound of Chemical Formula 36 ($R_3$=$CH_2CH_2OH$, $R_4$=$CO_2CH_2CH_2TMS$), which was obtained by reacting the ester of Chemical Formula 14 obtained in Reaction Scheme 3 with 1 equivalent of borane-methyl sulfide, is treated with sodium hydride-iodomethane, acetic anhydride, or methoxymethyl chloride, or methoxyethoxymethyl chloride and deprotected with tetrabutylammonium fluoride in dimethylsulfoxide, to provide a compound of Chemical Formula 41 ($R_3$=$CH_2CH_2OCH_3$), a compound of Chemical Formula 42 ($R_3$=$CH_2CH_2OAc$), a compound of Chemical Formula 43 ($R_3$=$CH_2CH_2OCH_2OCH_3$) and a compound of Chemical Formula 44 ($R_3$=$CH_2CH_2OCH_2OCH_2CH_2OCH_3$), respectively.

Meanwhile, the hydroxy group of the compound of Chemical Formula 36 is oxidized with tetrapropylammonium perruthenate to provide a compound of Chemical Formula 45 ($R_3$=$CH_2CHO$), which is condensed with methoxylamine, and deprotected with tetrabutylammonium fluoride in dimethylsulfoxide to give a compound of Chemical Formula 47 ($R_3$=$CH_2CHNOCH_3$).

The dose of the compound represented by Chemical Formula 1 is 0.01 to 1000 mg for an adult per one day as an defined as an anti-inflammatory analgesic agent, and the dose may be conventionally varied depending on age and body weight of the patient as well as the condition of symptoms.

The anti-inflammatory analgesic agent of the present invention may be formulated in proper forms which are suitable for oral administration or parenteral administration, according to the conventional processes for preparing formulations. In case of oral administration, the anti-inflammatory analgesic agent of the present invention may be prepared in the form of a tablet, capsule, solution, syrup, suspension, or the like, while in case of parenteral administration it may be prepared in the form of intraperitoneal, subcutaneous, intramuscular, or transcutaneous injection.

BEST MODE FOR CARRYING OUT THE INVENTION

The present invention is described in more detail with reference to the Examples. It should be noted that the scope of the present invention is not restricted in those Examples.

EXAMPLE 1

4-Hydroxymethyl-(−)-pimara-9(11),15-diene 101 mg of (−)-pimara-9(11),15-diene-4-carboxylic acid and 25.4 mg of lithium aluminum hydride were dissolved in 3 ml of ether and then stirred at room temperature for 10 hours. Some drops of methanol was added thereto to terminate the reaction. 20 ml of ether and 20 ml of a saturated solution of potassium sodium tartrate tetrahydrate were added to the reaction mixture, which was stirred vigorously at room temperature for 5 hours. The organic layer was washed with water and brine, dried over magnesium sulfate and then filtered. The filtrate was concentrated under reduced pressure to give a residue, which was then purified by silica gel column chromatography (eluent: ethyl acetate/hexane=⅕) to afford 82 mg of 4-hydroxymethyl-(−)-pimara-9(11),15-diene (85%).

IR(neat) : 3368 cm$^{-1}$ $^1$H—NMR (300 MHz, $CDCl_3$): 5.75(dd, 1H, J=17.5, 10.7 Hz), 5.29(m, 1H), 4.86(dd, 1H, J=17.5, 1.4 Hz), 4.79(dd, 1H, J=10.7, 1.4 Hz), 3.78(d, 1H, J=10.9 Hz), 3.47(d, 1H, J=10.9), 0.84–1.99(m, 16H), 0.097(s, 3H), 0.91(s, 3H), 0.90(s, 3H).

Mass (EI) m/e 288(M+)

EXAMPLE 2

4-Formyl-(−)-pimara-9(11),15-diene 55 mg of 4-hydroxymethyl-(−)-pimara-9(11),15-diene and catalytic amount of tetrapropylammonium perruthenate, 22.4 mg of N-methylmorpholine-N-oxide, and molecular sieve power were dissolved in 3 ml of chloromethane and then stirred at room temperature for 30 minutes. The reaction mixture was concentrated under reduced pressure, diluted with diethyl ether, and filtered with silica gel. The filtrate was concentrated under reduced pressure to give a residue, which was then purified by silica gel column chromatography (eluent: ethyl acetate/hexane=1/30) to afford 49 mg of 4-formyl-(−)-pimara-9(11),15-diene (91%).

IR(neat): 1717 cm$^{-1}$ $^1$H—NMR(300 MHz, CDCl$_3$) : 9.86(s, 1H), 5.75(dd, 1H, J=17.5, 10.7 Hz), 5.33(m, 1H), 4.87(dd, 1H, J=17.4, 1.4 Hz), 4.80(dd, 1H, J=10.7, 1.4 Hz), 0.86–1.99(m, 16H), 0.96(s, 3H), 0.90(s, 3H), 0.86(s, 3H)

Mass(EI) m/e 286(M+)

EXAMPLE 3

4-Methoxyvinyl-(−)-pimara-9(11),15-diene

To a solution of 23.5 mg of (methoxymethyl) triphenylphosphonium chloride in 2 ml of tetrahydrofuran, was slowly added a solution of 0.07 ml of potassium t-butoxide in tetrahydrofuran (1M) 16.3 mg of 4-formyl-(−)-pimara-9(11),15-diene prepared in the above Example 2 was dropwise added to the reaction mixture, which was then refluxed for 12 hours. The reaction mixture was concentrated under reduced pressure to give a residue, which was diluted with 20 ml of ethyl acetate and washed with water and brine. The reaction mixture was dried over magnesium sulfate and filtered. The filtrate was concentrated under reduced pressure to give a residue, which was then purified by silica gel column chromatography (eluent : ethyl acetate/hexane=1/30) to afford 19.8 mg of 4-methoxyvinyl-(−)-pimara-9(11),15-diene (90%, trans : cis=2:1).

trans isomer, $^1$H—NMR(300 MHz, CDCl$_3$):6.10(d, 1H, J=12.9 Hz), 5.75(dd, 1H, J=17.4, 10.7 Hz), 5.28(m, 1H), 5.01(d, 1H, J=13.1 Hz), 4.86(d, 1H, J=17.3 Hz), 4.79(d, 1H, J=10.7 Hz), 3.45(s,3H), 0.67–2.23(m, 25H).

cis isomer $^1$H—NMR(300 MHz, CDCl$_3$): 5.75(dd, 1H, J=17.4, 10.7 Hz), 5.63(d, 1H, J=7.3 Hz), 5.28(m, 1H), 4.86(d, 1H, J=17.3 Hz), 4.79(d, 1H, J=10.7 Hz), 4.35(d, 1H, J=7.1 Hz), 3.44(s,3H), 0.67–2.23(m, 25H)

EXAMPLE 4

4-Formylmethyl-(−)-pimara-9(11),15diene 7 mg of 4-methoxyvinyl-(−)-pimara-9(11),15-diene prepared in the above Example 3 and p-toluenesulfonic acid were dissolved in 2 ml of acetone and stirred at 0° C. for 30 minutes. 1 ml of a saturated solution of sodium carbonate was added to the reaction mixture, which was then diluted with 20 ml of ethyl acetate and washed with water and brine. The reaction mixture was dried over magnesium sulfate and filtered. The filtrate was concentrated under reduced pressure to give a residue, which was then purified by silica gel column chromatography (eluent : ethyl acetate/hexane=1/20) to afford 6.2 mg of 4-formylmethyl-(−)-pimara-9(11),15-diene (93%).

$^1$H—NMR(300MHz, CDCl$_3$) : 9.79(t, 1H, J=3.4 Hz), 5.77(dd, 1H, J=17.4, 10.5 Hz), 5.34(m, 1H), 4.86(dd, 1H, J=17.4, 1.4 Hz), 4.80(dd, 1H, J=10.6, 1.4 Hz), 0.76–2.53(m, 18H), 1.03 (s, 3H), 1.01(s, 3H), 0.90(s, 3H)

EXAMPLE 5

4-Carboxymethyl-(−)-pimara-9(11),15-diene

Silver nitrate and sodium hydroxide were dissolved in 2 ml of water and stirred at 0° C. for 1 hour. A solution of 15 mg of 4-formylmethyl-(−)-pimara-9(11),15-diene prepared in the above Example 4 in 1 ml of ethanol was added the reaction mixture, which was stirred for 9 hours and then filtered. The filtrate was extracted with 20 ml of ethyl acetate. The organic layer was washed with hydrochloric acid solution (0.5 M) and brine, dried over magnesium sulfate and filtered. The filtrate was concentrated under reduced pressure to give a residue, which was then purified by silica gel column chromatography (eluent : ethyl acetate/hexane=1/3) to afford 8 mg of 4-carboxymethyl-(−)-pimara-9(11),15-diene (51%)

IR(neat) : 3360(OH), 2923(CH), 1703(CO) cm$^{-1}$ $^1$H—NMR(300 MHz, CDCl$_3$) : 5.74(dd, 1H, J=17.5, 10.7 Hz), 5.28(m, 1H), 4.86(dd, 1H, J=17.4, 1.4 Hz), 4.80(dd, 1H, J=10.6, 1.4 Hz), 2.53(d, 1H, J=12.8 Hz), 2.23(d, 1H, J=12.8 Hz), 0.61–2.09(m, 16H), 0.99(s, 3H), 0.97(s, 3H), 0.90(s, 3H)

Mass(EI) m/e 316(M+)

EXAMPLE 6

4-Carboethoxyvinyl-(−)-pimara-9(11),15-diene 31.4 mg of triethyl phosphonoacetate and 4 mg of sodium hydride (60%) were dissolved in 1 ml of tetrahydrofuran and stirred at room temperature for 1 hour. A solution of 10 mg of 4-formyl-(−−)-pimara-9(11),15-diene prepared in the above Example 2 in 1 ml of tetrahydrofuran was added thereto and refluxed for 12 hours. The reaction mixture was diluted with 20 ml of ethyl acetate, washed with water and brine, dried over magnesium sulfate and filtered. The filtrate was concentrated under reduced pressure to give a residue, which was then purified by silica gel column chromatography (eluent : ethyl acetate/hexane=1/30) to afford 8.3 mg of 4-carboethoxyvinyl-(−−)-pimara-9(11),15-diene (70%).

$^1$H—NMR(300 MHz, CDCl$_3$) : 7.26(d, 1H, J=16.0 Hz), 5.75(dd, 1H, J=17.4, 10.7 Hz), 5.72(d, 1H, J=16.0 Hz), 5.28(m, 1H), 4.86(dd, 1H, J=17.4, 1.4 Hz), 4.79(dd, 1H, J=10.7, 1.4 Hz), 4.11(q, 2H, J=7.05 Hz), 0.65–2.10(m, 19H), 0.93(s, 3H), 0.90(s, 3H), 0.88(s, 3H)

EXAMPLE 7

4-Carboxyvinyl-(−)-pimara-9(11),15-diene 11 mg of 4-carboethoxyvinyl-(−)-pimara-9(11), 15-diene prepared in the above Example 6 was dissolved in a mixed solution of 1 ml of tetrahydrofuran and 1 ml of water. 3.9 mg of lithium hydroxide was added thereto and refluxed for 12 hours. The reaction mixture was diluted with water, acidified with hydrochloric acid solution (1 M), and then extracted with 20 ml of ethyl acetate. The organic layer was washed with hydrochloric acid solution (0.5 M) and brine, dried over magnesium sulfate and filtered. The filtrate was concentrated under reduced pressure to give a residue, which was purified by silica gel column chromatography (eluent: ethyl acetate/hexane=1/3) to afford 7.5 mg of 4-carboxyvinyl-(−)-pimara-9(11), 15-diene (75%).

$^1$H-NMR (300 MHz, CDCl$_3$): 7.37 (d, 1H, J=16.1 Hz), 5.74 (dd, 1H, J=17.5, 10.7 Hz), 5.72 (d, 1H, J=16.1 Hz), 5.29 (m, 1H), 4.86 (dd, 1H, J=17.4, 1.4 Hz), 4.80 (dd, 1H, J=10.7, 1.4 Hz), 0.71–2.28 (m, 16H), 0.95 (s, 3H), 0.90 (s, 3H), 0.88 (s, 3H)

EXAMPLE 8

4-Carbomethoxyethyl-(−)-pimara-9(11),15-diene 10 mg of 4-carboethoxyvinyl-(−)-pimara-9(11), 15-diene prepared in the above Example 6 was dissolved in 2 ml of methanol. 5 mg of magnesium powder was added thereto and stirred at room temperature for 12 hours. Hydrochloric acid solution (2 M) was added to the reaction mixture to dissolved the remaining magnesium. The reaction mixture was concentrated under reduced pressure and extracted with 20 ml of ethyl acetate. The organic layer was washed with water and brine, dried over magnesium sulfate, and filtered. The filtrate was concentrated under reduced pressure to give a residue, which was purified by silica gel column chromatography (eluent:ethyl acetate/hexane=1/30) to afford 9 mg of 4-carbomethoxyethyl-(−)-pimara-9(11), 15-diene (90%).

$^1$H NMR (300 MHz, CDCl$_3$):5.75 (dd, 1H, J=17.5, 10.7 Hz), 5.30 (m, 1H), 4.86 (dd, 1H, J=17.4, 1.4 Hz), 4.79 (dd, 1H, J=10.6, 1.4 Hz) 3.59 (s, 3H) 0.76–2.17 (m, 20H), 1.04 (s, 3H), 0.90 (s, 3H), 0.77 (s, 3H)

EXAMPLE 9

4-Carboxyethyl-(−)-pimara-9(11),15-diene 10 mg of 4-carbomethoxyethyl-(−)-pimara-9(11), 15-diene prepared in the above Example 8 was dissolved in a mixed solution of 1 ml of tetrahydrofuran and 1 ml of water. 3.9 mg of lithium hydroxide was thereto and refluxed for 12 hours. The reaction mixture was diluted with water, acidified with hydrochloric acid soltuion (1 M), extracted with 20 ml of ethyl acetate. The organic layer was washed with hydrochloric acid solution (0.5 M) and brine, dried over magnesium sulfate, and filtered. The filtrate was concentrated under reduced pressure to give a residue, which was purified by silica gel column chromatography (eluent:ethyl acetate/hexane=1/3) to afford 6.9 mg of 4-carboxyethyl-(−)-pimara-9(11), 15-diene (75%)

$^1$H-NMR (300 MHz, CDCl$_3$):5.75 (dd, 1H, J=17.5, 10.7 Hz), 5.33 (m, 1H), 4.86 (dd, 1H, J=17.5, 1.4 Hz), 4.79 (dd, 1H, J=10.7, 1.4 Hz), 0.71–2.31 (m, 20H) 1.04 (s, 3H), 0.90 (s, 3H), 0.80 (s, 1H)

EXAMPLE 10

4-Chloroformyl-(−)-pimara-9(11), 15-diene

To a solution of 10 mg of (−)-pimara-9(11), 15-diene-4-carboxylic acid in 2 ml of benzene, was added 30 μl of oxalyl chloride. The reaction mixture was stirred at room temperature for 1 hour and concentrated under reduced pressure to give unstable 4-chloroformyl-(−)-pimara-9(11), 15-diene.

EXAMPLE 11

4-Carbamoyl-(−)-pimara-9(11), 15-diene

The reaction mixture prepared in the above Example 10 was distilled under reduced pressure to give a residue, to which 1 ml of ammonia solution was added. To the reaction mixture, was added 2 ml of ethyl acetate and then stirred at room temperature for 30 minutes. The reaction mixture was extracted with 20 ml of ethyl acetate, washed with water and brine, dried over magnesium sulfate, and filtered. The filtrate was concentrated under reduced pressure to give a residue, which was purified by silica gel column chromatography (eluent:ethyl acetate/hexane=1:3) to afford 9.8 mg of 4-carbamoyl-(−)-pimara-9(11), 15-diene (99%).

$^1$H-NMR (300 MHz, CDCl$_3$):5.79 (dd, 1H, J=17.5, 10.7 Hz), 5.57 (s, 1H), 5.38 (m, 1H), 4.91 (dd, 1H, J=17.5, 1.4 Hz), 4.84 (dd, 1H, J=10.7, 1.4 Hz), 0.79–2.03 (m, 16H), 1.26 (s, 3H), 1.09 (s, 3H), 0.93 (s, 3H)

Mass(EI) m/e 301 (M+)

EXAMPLE 12

4-(N-methyl)carbamoyl-(−)-pimara-9(11), 15-diene

The reaction mixture prepared in the above Example 10 was distilled under reduced pressure to give a residue, to which 1 ml of methylamine solution was added. To the reaction mixture, was added 2 ml of ethyl acetate and then stirred at room temperature for 30 minutes. The reaction mixture was extracted with 20 ml of ethyl acetate. The organic layer was washed with water and brine, dried over magnesium sulfate, and filtered. The filtrate was concentrated under reduced pressure to give a residue, which was purified by silica gel column chromatography (eluent:ethyl acetate/hexane=1:3) to afford 10.3 mg of 4-(N-methyl) carbamoyl-(−)-pimara-9(11), 15-diene (99%)

$^1$H-NMR (300 MHz, CDCl$_3$):5.74 (dd, 1H, J=17.3, 10.7 Hz), 5.61 (s, 1H), 5.31 (m 1H), 4.86 (dd, 1H, J=17.4, 1.4 Hz), 4.80 (dd, 1H, J=10.7, 1.4 Hz), 2.71 (d, 3H, J=4.86), 0.78–2.12 (m, 16H), 1.12 (s, 3H), 0.89 (s, 3H), 0.88 (s, 3H)

Mass(EI) m/e 316 (M+)

EXAMPLE 13

4-Carbazoyl-(−)-pimara-9(11), 15-diene

The reaction mixture prepared in the above Example 10 was distilled under reduced pressure to give a residue, which was dissolved in 2 ml of dry ether. To the reaction mixture, was added 4.5 mg of hydrazine monohydrate at room temperature and then stirred at room temperature for 1 hour. The reaction mixture was extracted with 20 ml of dichloromethane. The organic layer was washed with water and brine, dried over magnesium sulfate, and filtered. The filtrate was concentrated under reduced pressure to give a residue, which was purified by silica gel column chromatography (eleunt:dichloromethane/methanol=30:1) to afford 10.3 mg of 4-carbazoyl-(−)-pimara-9(11), 15-diene (99%)

$^1$H-NMR (300 MHz, CDCl$_3$):6.91 (s, 1H), 5.74 (dd, 1H, J=17.5, 10.7 Hz), 5.32 (m, 1H), 4.86 (dd, 1H, J=17.5, 1.5 Hz), 4.80 (dd, 1H, J=10.7, 1.5 Hz), 0.71–2.25 (m, 16H), 1.15 (s, 3H), 0.92 (s, 3H), 0.77 (s, 3H)

Mass(EI) m/e 317(M+)

EXAMPLE 14

4-(N-hydroxy)carbaomyl-(−)-pimara-9(11), 15-diene

The reaction mixture prepared in the above Example 10 was distilled under reduced pressure to give a residue, to which 1 ml of benzene was added. To the reaction mixture, was added 4.5 mg of hydroxylamine hydrochloride at 0° C. and then stirred at room temperature for 3 hours. To the reaction mixture, was added 4 mg of dry sodium acetate. The reaction mixture was diluted with water and extracted with 20 ml of ethyl acetate. The organic layer was washed with water and brine, dried over magnesium sulfate, and filtered. The filtrate was concentrated under reduced pressure to give a residue, which was purified by silica gel column chromatography (eluent:ethyl acetate/hexane=1:1) to afford 10.4 mg of 4-(N-hydroxy)carbamoyl-(−)-pimara-9(11), 15-diene (99%)

$^1$H-NMR (300 MHz, CDCl$_3$):5.72 (dd, 1H, J=17.5, 10.7 Hz), 5.32 (m, 1H), 4.86 (d, 1H, J=17.5 Hz), 4.80 (d, 1H, J=10.7 Hz), 0.80–2.24 (m, 16H), 1.16 (s, 3H), 0.96 (s, 3H), 0.88 (s, 3H)

Mass(EI) m/e 316 M+)

EXAMPLE 15

16-Hydroxy-(−)-pimara-9(11)-en-4-carboxylic acid 0.6 ml of n-butyllithium (1.6 M) was added at −20° C. to a solution of 178 mg of (−)-pimara-9(11), 15-diene-4- carboxylic acid in 4 ml of tetrahydrofuran and stirred for 30 minutes. 0.5 ml of borane-methyl sulfide solution (2M) was added to the reaction mixture and then stirred at room temperature for 26 hours. 0.3 ml of sodium hydroxide solution (3N) and 0.3 ml of hydrogen peroxide solution (30%) were added to the reaction mixture, which was then stirred at room temperature for 3 hours. The reaction mixture was diluted with 50 ml of ethyl acetate, washed with hydrochloric acid solution (0.5 M) and brine, dried over magnesium sulfate and filtered. The filtrate was concentrated under reduced pressure to give a residue, which was purified by silica gel column chromatography (eluent:ethyl acetate/hexane=⅓) to afford 122.7 mg of 16-hydroxy-(−)-pimara-9(11)-en-4-carboxylic acid (68.5%)

IR(neat):3401 (OH), 2929 (CH), 1697 (CO) cm$^{-1}$ $^1$H-NMR (300 MHz, CDCl$_3$):5.29 (m, 1H), 3.67 (m, 2H), 0.70–2.15 (m, 18H), 1.16 (s, 3H), 0.92 (s, 3H), 0.87 (s, 3H)

Mass(EI) m/e 320 (M+)

EXAMPLE 16

16-Hydroxy-(−)-pimara-4-carboxylic acid 45 mg of 16-hydroxy-(−)-pimara-9(11)-en-4-carboxylic acid prepared in the above Example 15 was dissolved in 2 ml of dry methanol. Catalytic amount of palladium/active carbon (10%) was added thereto, substituted with hydrogen, and stirred at room temperature for 6 hours. The reaction mixture was concentrated under reduced pressure, diluted with diethyl ether, and filtered with silica gel. The filtrate was concentrated under reduced pressure to give a residue, which was purified by silica gel column chromatography (eluent:ethyl acetate/hexane=⅓) to afford 43 mg of 16-hydroxy-(−)-pimara-4-carboxylic acid (95%)

$^1$H-NMR (300 MHz, CDCl$_3$):3.67 (m, 2H), 0.69–2.10 (m, 20H), 1.19 (s, 3H), 0.83 (s, 3H), 0.77 (s, 3H)

EXAMPLE 17

2'-(Trimethylsily)ethyl (−)-pimara-9(11), 15-diene-4-carboxylate

The reaction mixture of Example 10 was distilled under reduced pressure to give a residue, to which was added 1 ml of pyridine and 0.02 ml of trimehtylsilylethanol. The reaction mixture was stirred at room temperature for 20 hours, diluted with 20 ml of ethyl acetate, washed with hydrochloric acid (1M), water and brine. The reaction mixture was dried over magnesium sulfate and filtered. The filtrate was concentrated under reduced pressure to give a residue, which was purified by silica gel column chromatography (eluent:ethyl acetate/hexane=1/30) to afford 11.3 mg of 2'-(trimethylsilyl)ethyl (−)-pimara-9(11), 15-diene-4-carboxylate (85%).

IR(neat):1718 (CO), 860 (Si(CH$_3$)$_3$) cm$^{-1}$ $^1$H-NMR (300 MHz, CDCl$_3$):5.77 (dd, 1H, J=10.7, 17.6 Hz), 5.34 (m, 1H), 4.88 (dd, 1H, J=1.5, 17.7 Hz), 4.82 (dd, 1H, J=1.5, 10.6 Hz), 4.08 (m, 2H), 0.81–2.13 (m, 18H), 1.14 (s, 3H), 0.91 (s, 3H), 0.83 (s, 3H), 0.00 (s, 9H)

Mass(EI) m/e 402 (M+)

EXAMPLE 18

2'-(Trimethylsilyl)ethyl 11,16-dihydroxy-(−)-pimara-4-carboxylate

To a solution of 10 mg of 2'-(trimethylsilyl)ethyl (−)-pimara-9(11), 15-diene-4-carboxylate prepared in the above Example 17 in 1.5 ml of tetrahydrofuran, was added 0.05 ml of borane-methyl sulfide (2M) at 0° C. The reaction mixture was stirred at room temperature for 20 hours. 0.1 ml of sodium hydroxide solution (3N) and 0.1 ml of hydrogen peroxide (30%) were added to the reaction mixture, which was then stirred at room temperature for 3 hours. The reaction mixture was diluted with 20 ml of ethyl acetate, washed with water and brine, dried over magnesium sulfate and filtered. The filtrate was concentrated under reduced pressure to give a residue, which was purified by silica gel column chromatography (eluent:ethyl acetate) to afford 6 mg of 2'-(trimethylsilyl)ethyl 11,16-dihydroxy-(−)-pimara-4-carboxylate (55%)

$^1$H-NMR(300 MHz, CDCl$_3$):4.05)m, 2H), 3.80 (dt, 1H, J=4.17, 10.5 Hz), 3.68 (t, 2H, J=7.5 Hz), 0.76–2.17 (m, 21H), 1.11 (s, 3H), 0.95 (s, 3H), 0.86 (s, 3H), 0.00 (s, 9H)

EXAMPLE 19

11,16-Dihydroxy-(−)-pimara-4-carboxylic acid

To a solution of 6 mg of 2'-(trimethylsily)ethyl 11,16-dihydroxy-(−)-pimara-4-carboxylate prepared in the above Example 18 in 1 ml of dimethylformamide, was added 0.06 ml of tetrabutylammonium fluoride. The reaction mixture was stirred at room temperature for 2 hours, diluted with 20 ml of ethyl acetate, washed with hydrochloric acid solution (0.5 M) and brine, dried over magnesium sulfate and then filtered. The filtrate was concentrated under reduced pressure to give a residue, which was purified by silica gel column chromatography (eluent:ethyl acetate) to afford 4.2 mg of 11,16-dihydroxy-(−)-pimara-4-carboxylic acid (91%)

$^1$H-NMR (300 MHz, CD$_3$OD):3.76 (dt, 1H, J=4.38, 10.71 Hz), 3.61 (t, 2H, J=7.8 Hz), 0.74–2.15 (m, 19H), 1.16 (s, 3H), 1.08 (s, 3H), 0.89 (s, 3H).

Mass(EI) m/e 339(M+)

EXAMPLE 20

2'-(Trimethylsilyl)ethyl 13-isoxazolinyl-(−)-pimara-9(11)-en-4-carboxylate

To a solution of 1170 mg of N-chlorosuccinimide in 8 ml of chloroform, were added 578 mg of acetaldoxime and 0.05 ml of pyridine. The reaction mixture was stirred at room temperature for 10 minutes. To the reaction mixture, was dropwise added a solution of 194 mg of 2'-(trimethylsilyl) ethyl (−)-pimara-9(11), 15-diene-4-carboxylate prepared in the above Example 17 in 3 ml of chloroform. While stirring the reaction mixture at 40° C., 1.34 ml of triethylamine was dropwise added to the reaction mixture for 30 minutes. The reaction mixture was stirred for 20 hours, diluted with 40 ml of chloroform, washed with hydrochloric acid solution (1M) and brine, dried over magnesium sulfate, and then filtered. The filtrate was concentrated under reduce pressure to give a residue, which was purified by silica gel column chromatography (eleuent:ethyl acetate/hexane=⅓) to afford 162 mg of 2'-(trimethylsilyl)ethyl 13-isoxazolinyl-(−)-pimara-9(11)-en-4-carboxylate (73%).

$^1$H-NMR (300 MHz, CDCl$_3$):5.32 (m, 1H), 4.19 (t, 1H, J=9.9 Hz), 4.08 (m, 2H), 2.71 (m, 2H), 0.74–2.23 (m, 18H), 1.92 (s, 3H), 1.13 (s, 3H), 0,87 (s, 3H), 0.79 (s, 3H), 0.00 (s, 9H)

EXAMPLE 21

13-Isoxazolinyl-(−)-pimara-9(11)-en-4-carboxylic acid

To a solution of 114 mg of 2'-(trimethylsilyl)ethyl 13-isoxazolinyl-(−)-pimara-9(11)-en-4-carboxylate prepared in the above Example 20 in 7 ml of dimethylformamide, was added 0.5 ml of tetrabutylammonium fluoride. The reaction mixture was stirred at room temperature for 2 hours, diluted with 50 ml of ethyl acetate, washed with hydrochloric acid solution (0.5 M) and brine, dried over magnesium sulfate, and then filtered. The filtrate was concentrated under reduced pressure to give a residue, which was purified by silica gel column chromatography (eluent:ethyl acetate/hexane=½) to afford 80 mg of 13-isoxazolinyl-(−)-pimara-9(11)-en-4-carboxylic acid (90%).

IR(neat):1692(CO) cm$^{-1}$ $^1$H-NMR(300 MHz, CDCl$_3$):5.35 (m, 1H), 4.21 (t, 1H, J=10.1 Hz), 2.73(m, 2H), 0.77–2.32(m, 16H), 1.94(s, 3H), 1.22(s, 3H), 0.95(s, 3H), 0.81(s, 3H)

Mass(EI) m/e 359(M+)

EXAMPLE 22

4-Carboethoxyallyl-(−)-pimara-9(11),15-diene 0.06 ml of triethyl phosphonoacetate and 12 mg of sodium hydride (60%) were dissolved in 1 ml of toluene and stirred for 1 hour. To the reaction mixture, was added a solution of 30 mg of 4-formylmethyl-(−)-pimara-9(11),15-diene prepared in the above Example 4 in 1 ml of toluene. The reaction mixture was stirred at room temperature for 1 hour, concentrated under reduced pressure to remove toluene, diluted with 20 ml of ethyl acetate, washed with water and brine, dried over magnesium sulfate, and then filtered. The filtrate was concentrated under reduced pressure to give a residue, which was purified by silica gel column chromatography (eluent:ethyl acetate/hexane=⅓₀) to afford 28 mg of 4-carboethoxyallyl-(−)-pimara-9(11),15-diene (76%).

$^1$H-NMR (300 MHz, CDCl$_3$):6.94 (td, 1H, J=7.8, 15.6 Hz), 5.79)m, 2H), 5.34(m, 1H), 4.91(dd, 1H, J=17.4, 1.2 Hz), 4.84(dd, J=10.7, 1.2 Hz), 4.16(q, 2H, J=7.3 Hz), 1.27(t, 3H, J=7.1 Hz), 0.80–2.49(m, 18H), 1.08(s, 3H), 0.95(s, 3H), 0.88(s, 3H)

EXAMPLE 23

4-Carboxyallyl-(−)-pimara-9(11),15-diene 13 mg of 4-carboethoxyallyl-(−)-pimara-9(11),15-diene prepared in the above Example 22 was dissolved in a mixed solution of 1 ml of tetrahydrofuran and 1 ml of water. 4.4 mg of lithium hydroxide monohydrate was added to the reaction mixture, which was refluxed for 12 hours and then diluted with 20 ml of ethyl acetate, washed with hydrochloric acid solution (0.5 M) and brine, dried over magnesium sulfate, and filtered. The filtrate was concentrated under reduced pressure to give a residue, which was purified by silica gel column chromatography (eluent:ethyl acetate/hexane=⅓) to afford 10.2 mg of 4-carboxyallyl-(−)-pimara-9(11),15-diene (85%).

$^1$H-NMR(300 MHz, CDCl$_3$):7.02(td, 1H, J=7.8, 15.6 Hz), 5.75(m, 2H), 5.30(m, 1H), 4.86(d, 1H, J=17.5 hz), 4.80(d, 1H, J=10.7 Hz), 0.69–2.48 (m, 18H), 1.04(s, 3H), 0.90(s, 3H), 0.84)s, 3H)

Mass(EI) m/e 342(M$^+$)

EXAMPLE 24

4-Carbomethoxypropyl-(−)-pimara-9(11),15-diene

To a solution of 15 mg of 4-carboethoxyallyl-(−)-pimara-9(11),15-diene prepared in the above Example 22 in 2 ml of methanol, was added 5 mg of magnesium powder. The reaction mixture was stirred at room temperature for 12 hours. Hydrochloric acid solution (2M) was added to the reaction mixture to dissolve the remaining magnesium. The reaction mixture was concentrated under reduced pressure to remove methanol and extracted with 20 ml of ethyl acetate. The organic layer was washed with water and brine, dried over magnesium sulfate, and filtered. The filtrate was concentrated under reduced pressure to give a residue, which was purified by silica gel column chromatography (eluent:ethyl acetate/hexane=⅓₀) to afford 12 mg of 4-carbomethoxypropyl-(−)-pimara-9(11),15-diene (83%).

$^1$H-NMR(300 MHz, CDCl$_3$):5.75(dd, 1H, J=17.5, 10.7 Hz), 5.27(m, 1H), 4.86)dd, 1H, J=17.4, 1.2 Hz), 4.79(dd, 1H, J=10.7, 1.2 Hz), 2.21(dt, 2H, J=2.0, 7.2 Hz), 0.74–1.99 (m, 20H), 1.00(s, 3H), 0.90(s, 3H), 0.79(s, 3H)

EXAMPLE 25

4-Carboxypropyl-(−)-pimara-9(11),15-diene 10 mg of 4-caromethoxypropyl-(−)-pimara-9(11),15-diene prepared in the above Example 24 was dissolved in a mixed solution of 1 ml of tetrahydrofuran and 1 ml of water. 3.5 mg of lithium hydroxide monohydrate was added to the reaction mixture, which was refluxed for 4 hours and diluted with 20 ml of ethyl acetate, washed with hydrochloric acid solution (0.5 M) and brine, dried over magnesium sulfate, and filtered. The filtrate was concentrated under reduced pressure to give a residue, which was purified by silica gel column chromatography (eluent:ethyl acetate/hexane=⅓) to afford 6 mg of 4-carboxypropyl-(−)-pimara-9(11),15-diene (62.4%)

$^1$H-NMR(300 MHz, CDCl$_3$):5.80(dd, 1H, J=17.5, 10.7 Hz), 5.32(m, 1H), 4.91(dd, 1H, J=17.3, 1.5 Hz), 4.84(dd, 1H, J=10.7, 1.5 Hz), 0.70–2.35 (m, 22H), 1.06(s, 3H), 0.95(s, 3H), 0.84(s, 3H)

Mass(EI) m/e 344(M$^+$)

EXAMPLE 26

4-Hydroxymethylvinyl-(−)-pimara-9(11),15-diene

To a solution of 24 mg of 4-carboethoxyvinyl-(−)-pimara-9(11),15-diene prepared in the above Example 6 in 2 ml of dichloromethane, was added 0.15 ml of diisobutylaluminum hydride solution (1M) at −78° C. After the reaction mixture was stirred for 30 minutes, some drops of methanol was added thereto to terminate the reaction. 20 ml of dichloromethane and 20 ml of a saturated solution of potassium sodium tartrate tetrahydrate were added to the reaction mixture, which was stirred vigorously at room temperature for 2 hours. The organic layer was washed with water and brine, dried over magnesium sulfate, and filtered. The filtrate was concentrated under reduced pressure to afford 20 mg of 4-hydroxymethylvinyl-(−)-pimara-9(11),15-diene (95%).

IR(neat):3331(OH), 2924(CH) cm$^{-1}$

Mass(EI) me/ 314(M$^+$)

EXAMPLE 27

4-Formylvinyl-(−)-pimara-9(11),15-diene 20 mg of 4-hydroxymethylvinyl-(−)-pimara-9(11),15-diene prepared in the above Example 26, catalytic amount of tetrapropylammonium perruthenate, 12 mg of N-methylmorpholine-N-oxide, and molecular sieve powder were dissolved in 2 ml of dichloromethane and then stirred at room temperature for 1 hour. The reaction mixture was concentrated under reduced pressure, diluted with diethyl ether, and filtered with silica gel. The filtrate was concentrated under reduced pressure to give a residue, which was purified by silica gel column chromatography (eluent:ethyl acetate/hexane=1/30) to afford 17 mg of 4-formylvinyl-(−)-pimara-9(11),15-diene (85.5%).

IR(neat):2924)CH), 1691(CO) cm$^{-1}$

Mass(EI) m/e 312(M$^+$)

EXAMPLE 28

4-Carboethoxybutadienyl-(−)-pimara-9(11),15-diene

69 μl of triethyl phosphonoacetate and 13.4 mg of sodium hydride (60%) were dissolved in 1.5 ml of tetrahydrofuran and then stirred at room temperature for 1 hour. A solution of 35 mg of 4-formylvinyl-(−)-pimara-9(11),15-diene prepared in the above Example 27 in 1 ml of tetrahydrofuran was added to the reaction mixture, which was stirred at room temperature for 30 minutes. The reaction mixture was concentrated under reduced pressure to remove tetrahydrofuran, diluted with 20 ml of ethyl acetate, washed with water and brine, dried over magnesium sulfate, and then filtered. The filtrate was concentrated under reduced pressure to give a residue, which was purified by silica gel column chromatography (eluent:ethyl acetate/hexane=1/30) to afford 41 mg of 4-carboethoxybutadienyl-(−)-pimara-9(11),15-diene (95.7%).

$^1$H-NMR(500 MHz, CDCl$_3$):7.23(dd, 1H, J=15.7, 10.6 Hz), 6.39(d, 1H, J=15.7 Hz), 6.06(dd, 1H, J=15.6, 10.9 HZ), 5.74(m, 2H), 5.29(m, 1H), 4.86(dd, 1H, J=17.5, 1.3 Hz), 4.79(dd, 1H, J=10.7, 1.3 Hz), 4.13(q, 2H, J=7.14 Hz), 0.61–2.24(m, 16H), 1.22(t, 3H, J=5.73 Hz), 0.93(s, 3H), 0.91(s, 3H), 0.88(s, 3H)

EXAMPLE 29

4-Carboxybutadienyl-(−)-pimara-9(11),15-diene 41 mg of 4-carboethoxybutadienyl-(−)-pimara-9(11),15-diene prepared in the above Example 28 was dissolved in a mixed solution of 1 ml of tetrahydrofuran and 1 ml of water. 13.5 mg of lithium hydroxide monohydrate was added to the reaction mixture, which was refluxed for 12 hours and diluted with 20 ml of ethyl acetate, washed with hydrochloric acid solution (0.5 M) and brine, dried over magnesium sulfate, and then filtered. The filtrate was concentrated under reduced pressure to give a residue, which was purified by silica gel column chromatography (eluent:ethyl acetate/hexane=1/3) to afford 33.5 mg of 4-carboxybutadienyl-(−)-pimara-9(11),15-diene (88%).

IR(neat): 3440(OH), 2920(CH), 1683(CO) cm$^{-1}$ $^1$H-NMR(500 MHz, CDCl$_3$):7.39(dd, 1H, J=15.3, 10.8 Hz), 6.52(d, 1H, J=15.6 Hz), 6.17(dd, 1H, J=15.6, 11.0 Hz), 5.81 (m, 2H), 5.36(m, 1H), 4.93(dd, 1H, J=17.5, 1.4 Hz), 0.68–2.36(m, 16H), 1.00(s, 3H), 0.97(s, 3H), 0.95(s, 3H)

Mass(EI) m/e 354(M$^+$)

EXAMPLE 30

4-Hydroxypropyl-(−)-pimara-9(11),15-diene

To a solution of 40 mg of 4carbomethoxyethyl-(−)-pimara-9(11),15-diene prepared in the above Example 8 in 2 ml of dichloromethane, was added 0.25 ml of diisobutylaluminum hydride solution (1M) at −78° C. After the reaction mixture was stirred for 30 minutes, some drops of methanol was added thereto to terminate the reaction. 20 ml of dichloromethane and 20 ml of a saturated solution of potassium sodium tartrate tetrahydrate were added to the reaction mixture, which was vigorously stirred at room temperature for 2 hours. The organic layer was washed with water and brine, dried over magnesium sulfate, and filtered. The filtrate was concentrated under reduced pressure to give a residue, which was purified by silica gel column chromatography (eluent:ethyl acetate/hexane=1/3) to afford 36 ml of 4-hydroxypropyl-(−)-pimara-9(11),15-diene (98%).

IR(neat): 3322(OH), 2922(CH) cm$^{-1}$

Mass(EI) m/e 316(M$^+$)

EXAMPLE 31

4-Formylethyl-(−)-pimara-9(11),15-diene 36 mg of 4-hydroxypropyl-(−)-pimara-9(11),15-diene prepared in the above Example 30, catalytic amount of tetrapropylammonium perruthenate, 20 mg, of N-methylmorpholine-N-oxide, and molecular sieve powder were dissolved in 2 ml of dichloromethane and then stirred at room temperature for 1 hour. The reaction mixture was concentrated under reduced pressure, diluted with diethyl ether, and filtered with silica gel. The filtrate was concentrated under reduced pressure to afford 4-formylethyl-(−)-pimara-9(11),15-diene, which was proceeded to the reaction of Example 32.

EXAMPLE 32

4-Carboethoxyhomoallyl-(−−)-pimara-9(11),15-diene

60 μl of triethyl phosphonoacetate and 12 mg of sodium hydride (60%) were dissolved in 1.5 ml of tetrahydrofuran and then stirred at room temperature for 1 hour. A solution of 35 mg of 4-formylethyl-(−)-pimara-9(11)15-diene prepared in the above Example 31 in 1 ml of tetrahydrofuran was added to the reaction mixture, which was stirred at room temperature for 30 minutes. The reaction mixture was concentrated under reduced pressure to remove tetrahydrofuran, diluted with 20 ml of ethyl acetate, washed with water and brine, dried over magnesium sulfate, and then filtered. The filtrate was concentrated under reduced pressure to afford 4-carboethoxyhomoallyl-(−)-pimara-9(11),15-diene, which was proceeded to the reaction of Example 33.

EXAMPLE 33

4-Carboxyhomoallyl-(−)-pimara-9(11),15-diene 18 mg of 4-carboethoxyhomoallyl-(−)-pimara-9(11),15-diene prepared in the above Example 32 was dissolved in a mixed solution of 1 ml of tetrahydrofuran and 1 ml of water. 6 mg of lithium hydroxide monohydrate was added to the reaction mixture, which was refluxed for 4 hours and diluted with 20 ml of ethyl acetate, washed with hydrochloric acid solution (0.5 M) and brine, dried over magnesium sulfate, and filtered. The filtrate was concentrated under reduced pressure to give a residue, which was purified by silica gel column chromatography (eluent:ethyl acetate/hexane=1/3) to afford 13.5 mg of 4-carboxyhomoallyl-(−)-pimara-9(11),15-diene (81%).

$^1$H-NMR(300 MHz, CDCl$_3$):7.03)dtd, 1H, J=2.7, 6.8, 15.6 Hz), 5.75(m, 2H), 5.28(m, 1H), 4.86(dd, 1H, J=17.4, 1.2 Hz), 4.79(dd, 1H, J=10.6, 1.2 Hz), 0.71–2.06(m, 20 H), 1.02(s, 3H), 0.90(s, 3H), 0.81(s, 3H)

Mass(EI) m/e 356(M$^+$)

EXAMPLE 34

4-Carbomethoxybutyl-(–)-pimara-9(11),15-diene

To a solution of 18 mg of 4-carboethoxyhomoallyl-(–)-pimara-9(11),15-diene prepared in the above Example 32 in 2 ml of methanol, was added 5 mg of magnesium powder. The reaction mixture was stirred at room temperature for 12 hours. Hydrochloric acid solution (2M) was added to the reaction mixture to dissolve the remaining magnesium. The reaction mixture was concentrated under reduced pressure to remove methanol and extracted with 20 ml of ethyl acetate. The organic layer was washed with water and brine, dried over magnesium sulfate, and filtered. The filtrate was concentrated under reduced pressure to give 4-carbomethoxybutyl-(–)-pimara-9(11),15-diene, which are proceeded to the reaction of Example 35.

EXAMPLE 35

4-Carboxybutyl-(–)-pimara-9(11),15-diene 16 mg of 4-carbomethoxybutyl-(–)-pimara-9(11),15-diene prepared in the above Examples 34 was dissolved in a mixed solution of 1 ml of tetrahydrofuran and 1 ml of water. 5 mg of lithium hydroxide monohydrate was added to the reaction mixture, which was refluxed for 4 hours and diluted with 20 ml of ethyl acetate, washed with hydrochloric acid solution (0.5 M) and brine, dried over magnesium sulfate, and then filtered. The filtrate was concentrated under reduced pressure to give a residue, which was purified by silica gel column chromatography (eluent:ethyl acetate/hexane=⅓) to afford 14.5 mg of 4-carboxybutyl-(–)-pimara-9(11),15-diene (94%).

$^1$H-NMR(300 MHz, CDCl$_3$): 5.75(dd, 1H, J=17.5, 10,7 Hz), 5.27(m, 1H), 4.86(dd, 1H, J=17.4, 1.4 Hz), 4.79(dd, 1H, J=10.7, 1.4 Hz), 2.29(dt, 2H, J=2.4, 7.4 Hz), 0.68–1.98 (m, 22H), 1.01(s, 3H), 0.90(s, 3H), 0.76(s, 3H)

Mass(EI) m/e 358(M$^+$)

EXAMPLE 36

Pipsylamide 2 ml of ammonia solution was added to 15 mg of pipsyl chloride and then stirred at room temperature for 5 minutes. The reaction mixture was diluted with ethyl acetate. The organic layer was washed with water and brine, dried over magnesium sulfate and filtered. The filtrate was concentrated under reduced pressure to give 11.2 mg of pipsylamide (80%) as a white solid form.

IR(neat):3351(NH), 816(CI) cm$^{-1}$ $^1$H-NMR(300 MHz, CDCl$_3$): 7.81(d, 2H, J=8.28), 7.57(d, 2H, J=8.04 Hz), 4.74(s, 1H)

Mass(EI) m/e 283(M+)

EXAMPLE 37

4-Chloroformylmethyl-(–)-pimara-9(11),15-diene

To a solution of 10 mg of 4-carboxymethyl-(–)-pimara-9(11),15-diene prepared in the above Example 5 in 2 ml of benzene, was added 30 μl of oxalyl chloride. The reaction mixture was stirred at room temperature for 1 hour and concentrated under reduced pressure to give unstable 4-chloroformylmethyl-(–)-pimara-9(11),15-diene.

EXAMPLE 38

4-(N-pipsyl)carbamoylmethyl-(–)-pimara-9(11),15-diene 9.6 mg of pipsylamide prepared in the above Example 36 and 1.4 mg of sodium hydride (60%) were dissolved in 1 ml of tetrahydrofuran and stirred at room temperature for 30 minutes (Reaction Mixture A). The reaction mixture prepared in the above Example 37 was concentrated under reduced pressure to give a residue, which was then dissolved in 1 ml of tetrahydrofuran (Reaction Mixture B). Reaction Mixture B was added to Reaction Mixture A and stirred at room temperature for 1 hour. The reaction mixture was concentrated under reduced pressure to remove tetrahydrofuran, diluted with 20 ml of dichloromethane, washed with water and brine, dried over magnesium sulfate, and then filtered. The filtrate was concentrated under reduced pressure to give a residue, which was purified by silica gel column chromatography (eluent:ethyl acetate/hexane=1:5) to afford 17 mg of 4-(N-pipsyl)carbamoylmethyl-(–)-pimara-9(11),15-diene (92%).

IR(neat):3434(NH), 2922(CH), 1715(CO) cm$^{-1}$ $^1$H-NMR(300 MHz, CDCl$_3$):7.84(d, 2H, J=8.8 Hz), 7.69 (d, 2H, J=8.5 Hz), 5.73(dd, 1H, J=17.5, 10.7 Hz), 5.29(m, 1H), 4.85(d, 1H, J=17.5 Hz), 4.79(d, 1H, J=10.5), 0.82–2.36 (m, 18H), 0.91(s, 3H), 0.88(s, 3H), 0.85(s, 3H)

Mass(EI) me/ 581(M$^+$)

EXAMPLE 39

4-Chloroformylethyl-(–)-pimara-9(11),15-diene

To a solution of 10 mg of 4-carboxyethyl-(–)-pimara-9(11),15-diene prepared in the above Example 9 in 2 ml of benzene, was added 30 μl, of oxalyl chloride. The reaction mixture was stirred at room temperature for 1 hour and concentrated under reduced pressure to give unstable 4-chloroformylethyl-(–)-pimara-9(11),15-diene.

EXAMPLE 40

4-(N-pipsyl)carbamoylethyl-(–)-pimara-9(11),15-diene 9.6 mg of pipsylamide prepared in the above Example 36 and 1.4 mg of sodium hydride (60%) were dissolved in 1 ml of tetrahydrofuran and stirred at room temperature for 30 minutes (Reaction Mixture A). The reaction mixture prepared in the above Example 39 was concentrated under reduced pressure to give a residue, which was then dissolved in 1 ml of tetrahydrofuran (Reaction Mixture B). Reaction Mixture B was added to Reaction Mixture A and stirred at room temperature for 1 hour. The reaction mixture was concentrated under reduced pressure to remove tetrahydrofuran, diluted with 20 ml of dichloromethane, washed with water and brine, dried over magnesium sulfate, and then filtered. The filtrate was concentrated under reduced pressure to give a residue, which was purified by silica gel column chromatography (eluent:ethyl acetate/hexane=1:5) to afford 16.2 mg of 4-(N-pipsyl)carbamoylethyl-(–)-pimara-9(11),15-diene (90%).

$^1$H-NMR(300 MHz, CDCl$_3$):8.21(s, 1H), 7.85(d, 2H, J=8.5 Hz), 7.71(d, 2H, J=8.5 Hz), 5.74(dd, 1H, J=17.4, 10.4 Hz), 5.27(m, 1H), 4.85(dd, 1H, J=17.4, 1.2Hz), 4.79(dd, 1H, J=10.7, 1.2Hz), 0.64–2.20(m, 20H), 0.98(s, 3H), 0.88(s, 3H), 0.70(s, 3H)

Mass(EI) m/e 595(M$^+$)

EXAMPLE 41

4-(N-methanesulfonyl)carbamoylethyl-(–)-pimara-9(11),15-diene 6 mg of methanesulfonamide and 2.5 mg of sodium hydride (60%) were dissolved in 1 ml of tetrahydrofuran and stirred at room temperature for 30 minutes (Reaction Mixture A). The reaction mixture prepared in the above Example 39 was concentrated under reduced pressure to give a residue, which was then dissolved in 1 ml of tetrahydrofuran (Reaction Mixture B). Reaction Mixture B was added to reaction Mixture A and stirred at room temperature for 1 hour. The reaction mixture was concentrated under reduced pressure to remove tetrahydrofuran, diluted with 20 ml of ethylacetate, washed with water and brine, dried over magnesium sulfate, and then filtered. The filtrate was concentrated under reduced pressure to give a residue, which was purified by silica gel column chromatography (eluent:ethyl acetate/hexane=1:3) to afford 9.2 mg of 4-(N-methanesulfonyl)carbaomylethyl-(−)-pimara-9(11),15-diene (75%).

$^1$H-NMR(300 MHz, CDCl$_3$):8.34(s, 1H), 5.75(dd, 1H, J=17.4, 10.7 Hz), 5.29(m, 1H), 4.86(d, 1H, J=17.4 Hz), 4.79(d, 1H, J=10.6 Hz), 3.24(s, 3H), 0.77–2.29(m, 20H), 1.04(s, 3H), 0.90(s, 3H), 0.78(s, 3H)

EXAMPLE 42

4-Chloroformylbutadienyl-(−)-Pimara-9(11),15-Diene

To a solution of 12 mg of 4-carboxybutadienyl-(−)-pimara-9(11),15-diene prepared in the above Example 29 in 2 ml of benzene, was added 30 μl of oxalyl chloride. The reaction mixture was stirred at room temperature for 1 hour and concentrated under reduced pressure to give unstable 4-chloroformylbutadienyl-(−)-pimara-9(11), 15-diene.

EXAMPLE 43

4-(N-Pipsyl)Carbamoylbutadienyl-(−)-Pimara-9(11), 15-Diene 9.6 mg of pipsylamide prepared in the above Example 36 and 1.4 mg of sodium hydride (60%) were dissolved in 1 ml of tetrahydrofuran and stirred at room temperature for 30 minutes (Reaction Mixture A). The reaction mixture prepared in the above Example 42 was concentrated under reduced pressure to give a residue, which was then dissolved in 1 ml of tetrahydrofuran (Reaction Mixture B). Reaction Mixture B was added to Reaction Mixture A and stirred at room temperature for 1 hour. The reaction mixture was concentrated under reduced pressure to remove tetrahydrofuran, diluted with 20 ml of dichloromethane, washed with water and brine, dried over magnesium sulfate, and then filtered. The filtrate was concentrated under reduced pressure to give a residue, which was purified by silica gel column chromatography (eluent: ethyl acetate/hexane=1:3) to afford 10 mg of 4-(N-pipsyl)carbamoylbutadienyl-(−)-pimara-9(11),15-diene (48%).

$^1$H-NMR (300 MHz, CDCl$_3$): 8.41(s, 1H), 7.83(d, 2H, J=8.5 Hz), 7.72(d, 2H, J=8.3 Hz), 7.26(m, 1H), 6.47(d, 1H, J=15.6 Hz), 6.04(dd, 1H, J=15.6, 10.7 Hz), 5.71(m, 2H), 5.28(m, 1H), 5.28(m, 1H), 4.86(dd, 1H, J=17.4, 1.2 Hz), 4.79(dd, 1H, J=10.7, 1.2 Hz), 0.71–2.25(m, 16H), 0.90(s, 3H), 0.89(s, 3H), 0.81(s, 3H)

Mass (EI) m/e 619(M$^+$)

EXAMPLE 44

2'-(Trimethylsilyl)Ethyl 16-Hydroxy-(−)-Pimara-9(11)-En-4-Carboxylate

To a solution of 73 mg of 2'-(trimethylsilyl)ethyl (−)-pimara-9(11), 15-diene-4-carboxylate prepared in the above Example 17 in 5 ml of tetrahydrofuran, was added 0.33 ml of borane-methyl sulfide solution (2M) at 0° C. The reaction mixture was stirred at 0° C. for 60 hours. 0.3 ml of sodium hydroxide solution (3N) and 0.3 ml of hydrogen peroxide (30%) were added to the reaction mixture, which was then stirred at room temperature for 1 hour. The reaction mixture was concentrated under reduced pressure to remove tetrahydrofuran, diluted with 20 ml of ethyl acetate, washed with water and brine, dried over magnesium sulfate, and then filtered. The filtrate was concentrated under reduced pressure to give a residue, which was purified by silica gel column chrmatography (eluent: ethyl acetate/hexane=⅕) to afford 24 mg of 2'-(trimethylsilyl)ethyl 16-hydroxy-(−)-pimara-9(11)-en-4-carboxylate (32%).

$^1$H-NMR(300 MHz, CDCl$_3$): 5.30(m, 1H), 4.08(m, 2H), 3.69(m, 2H), 0.78–2.25(m, 20H), 1.13(s, 3H), 0.87(s, 3H), 0.83(s, 3H), 0.00(s, 9H)

EXAMPLE 45

2'-(Trimethylsilyl)Ethyl 16-Methoxy-(−)-Pimara-9(11)-En-4-Carboxylate 1.8 ml of diethyl ether and 0.2 ml of dimethylsulfoxide were added to 2.5 mg of sodium hydride (60%). While stirring the reaction mixture at room temperature, a solution of 13 mg of 2'-(trimethylsilyl)ethyl 16-hydroxy-(−)-pimara-9(11)-en-4-carboxylate prepared in the above Example 44 in 0.5 ml of diethyl ether was added thereto. After 30 minutes, 10 μl of iodomethane was added to the reaction mixture, which was stirred for 2 hours. The reaction mixture was diluted with 20 ml of diethyl ether, washed with water and brine, dried over magnesium sulfate, and filtered. The filtrate was concentrated under reduced pressure to give a residue, which was purified by silica gel column chromatography (eluent: ethyl acetate/hexane=1/30) to afford 10 mg of 2'-(trimethylsilyl)ethyl 16-methoxy-(−)-pimara-9(11)-en-4-carboxylate (74%).

$^1$H-NMR(300 MHz, CDCl$_3$): 5.30(m, 1H), 4.08(m, 2H), 3.40(m, 2H), 3.28(s, 3H), 0.78–2.17(m, 20H), 1.13(s, 3H), 0.87(s, 3H), 0.82(s, 3H), 0.00(s, 9)

EXAMPLE 46

16-Methoxy-(−)-Pimara-9(11)-En-4-Carboxylic Acid

To a solution of 20 mg of 2'-(trimethylsilyl)ethyl 16-methoxy-(−)-pimara-9(11)-en-4-carboxylate prepared in the above Example 45 in 1 ml of dimethylsulfoxide, was added 0.15 ml of tetrabutylammonium fluoride solution (1M). The reaction mixture was stirred at room temperature for 10 minutes, diluted with 20 ml of ethyl acetate, washed with hydrochloric acid solution (0.5M) and brine, dried over magnesium sulfate, and then filtered. The filtrate was concentrated under reduced pressure to give a residue, which was purified by silica gel column chromatography (eluent: ethyl acetate/hexane=⅛) to afford 12 mg of 16-methoxy-(−)-pimara-9(11)-en-4-carboxylic acid (78%).

$^1$H-NMR(300 MHz, CDCl$_3$): 5.29(m, 1H), 3.38(m, 2H), 3.25(s, 3H), 0.58–2.19(m, 18H), 1.17(s, 3H), 0.91(s, 3H), 0.79(s, 3H)

Mass(EI) m/e 334(M$^+$)

EXAMPLE 47

2'-(Trimethylsilyl)Ethyl 16-Acetyloxy-(−)-Pimara-9(11)-En-4-Carboxylate 23 mg of 2'-(trimethylsilyl)ethyl 16-hydroxy-(−)-pimara-9(11)-en-4-carboxylate prepared in the above Example 44 was dissolved in 2 ml of pyridine. 20 µl of acetic anhydride was added to the reaction mixture, which was then stirred at room temperature for 3 hours. 1 ml of water was added to the reaction mixture, which was stirred for 20 minutes, diluted with 20 ml of ethyl acetate, and then washed with a saturated solution of sodium carbonate, hydrochloric acid solution (0.5M), and brine. The reaction mixture was dried over magnesium sulfate and filtered. The filtrate was concentrated under reduced pressure to give a residue, which was purified by silica gel column chromatography (eluent: ethyl acetate/hexane=1/30) to afford 21 mg of 2'-(trimethylsilyl)ethyl 16-acetyloxy-(−)-pimara-9(11)-en-4-carboxylate (83%).

$^1$H-NMR(300 MHz, CDCl$_3$): 5.30(m, 1H), 4.08(m, 4H), 0,73–2.22(m, 20H), 1.99(s, 3H), 1.13(s, 3H), 0.87(s, 3H), 0.84(s, 3H), 0.00(s, 9H).

EXAMPLE 48

16-Acetyloxy-(−)-Pimara-9(11)-En-4-Carboxylic Acid

To a solution of 21 mg of 2'-(trimethylsilyl)ethyl 16-acetyloxy-(−)-pimara-9(11)-en-4-carboxylate prepared in the above Example 47 in 1 ml of dimethylsulfoxide, was added 0.15 ml of tetrabutylammonium fluoride solution (1M). The reaction mixture was stirred at room temperature for 30 minutes, diluted with 20 ml of ethyl acetate, washed with hydrochloric acid solution (0.5M) and brine. The reaction mixture was dried over magnesium sulfate and filtered. The filtrate was concentrated under reduced pressure to give a residue, which was purified by silica gel column chromatography (eluent: ethyl acetate/hexane=1/8) to afford 14 mg of 16-acetyloxy-(−)-pimara-9(11)-en-4-carboxylic acid (82%).

$^1$H-NMR(300 MHz, CDCl$_3$): 5.28(m, 1H), 4.08(t, 2H, J=7.8 Hz), 0.68–2.21(m, 18H), 1.97(s, 3H), 1.17(s, 3H), 0.92(s, 3H), 0.82(s, 3H)

Mass(EI) m/e 362(m$^+$)

EXAMPLE 49

2'-(Trimethylsilyl)Ethyl 16-Methoxymethoxy-(−)-Pimara-9(11)-En-4-Carboxylate

To a solution of 15 mg of 2'-(trimethylsilyl)ethyl 16-hydroxy-(−)-pimara-9(11)-en-4-carboxylate prepared in the above Example 44 in 2 ml of dichloromethane, were added 13 µl of diisopropylethylamine and 6 µl of methoxymethyl chloride. The reaction mixture was stirred at room temperature for 1 hour, diluted with 20 ml of dichloromethane, and washed with a saturated solution of ammonium chloride, water and brine. The reaction mixture was dried over magnesium sulfate and filtered. The filtrate was concentrated under reduced pressure to give a residue, which was then was purified by silica gel column chromatography (eluent: ethyl acetate/hexane=1/30) to afford 11.5 mg of 2'-(trimethylsilyl)ethyl 16-methoxymethoxy-(−)-pimara-9(11)-en-4-carboxylate (69%).

$^1$H-NMR(300 MHz, CDCl$_3$): 5.30(m, 1H), 4.08(t, 2H, J=7.8 Hz), 4.08(m, 2H), 3.55(dt, 2H, J=2.9, 7.5 Hz), 3.32(s, 3H), 0.78–2.25(m, 20H), 1.13(s, 3H), 0.87(s, 3H), 0.83(s, 3H) 0.00(s, 9H)

EXAMPLE 50

16-Methoxymethoxy-(−)-Pimara-9(11)-En-4-Carboxylic Acid

To a solution of 22.5 mg of 2'-(trimethylsilyl)ethyl 16-methoxymethoxy-(−)-pimara-9(11)-en-4-carboxylate prepared in the above Example 49 in 1 ml of dimethylsulfoxide, was added 0.15 ml of tetrabutylammonium fluoride solution (1M). The reaction mixture was stirred at room temperature for 1 hour, diluted with 20 ml of ethyl acetate, washed with hydrochloric acid solution (0.5M) and brine. The reaction mixture was dried over magnesium sulfate and filtered. The filtrate was concentrated under reduced pressure to give a residue, which was purified by silica gel column chromatography (eluent: ethyl acetate/hexane=1/5) to afford 14 mg of 16-methoxymethoxy-(−)-pimara-9(11)-en-4-carboxylic acid (76%).

$^1$H-NMR(300 MHz, CDCl$_3$): 5.29(m, 1H), 4.55(s, 2H), 3.53(dt, 2H, J=2.9, 7.5 Hz), 3.29(s, 3H), 0.74–2.24(m, 18H), 1.17(s, 3H), 0.91(s, 3H), 0.80(s, 3H)

Mass(EI) m/e 364(M$^+$)

EXAMPLE 51

2'-(Trimethylsilyl)Ethyl 16-Methoxyethoxymethoxy-(−)-Pimara-9(11)-En-4-Carboxylate To a solution of 18 mg of 2'-(trimethylsilyl)ethyl 16-hydroxy-(−)-pimara-9(11)-en-4-carboxylate prepared in the above Example 44 in 2 ml of dichloromethane, were added 16 µl of diisopropylethylamine and 10 µl of methoxyethoxymethyl chloride. The reaction mixture was stirred at room temperature for 2 hours, diluted with 20 ml of dichloromethane, and washed with a saturated solution of ammonium chloride, water and brine. The reaction mixture was dried over magnesium sulfate and filtered. The filtrate was concentrated under reduced pressure to give a residue, which was then was purified by silica gel column chromatography (eluent: ethyl acetate/hexane=1/10) to afford 14.5 mg of 2'-(trimethylsilyl)ethyl 16-methoxyethoxymethoxy-(−)-pimara-9(11)-en-4-carboxylate (66%).

$^1$H-NMR(300 MHz, CDCl$_3$): 5.30(m, 1H), 4.66(s, 2H), 4.08(m, 2H), 3.59(m, 6H), 3.36(s, 3H), 0.72–2.24(m, 20H), 1.13(s, 3H), 0.87(s, 3H), 0.82(s, 3H), 0.00(s, 9H)

EXAMPLE 52

16-Methoxyethoxymethoxy-(−)-Pimara-9(11)-En-4-Carboxylic Acid

To a solution of 14.5 mg of 2'-(trimethylsilyl)ethyl 16-methoxyethoxymethoxy-(−)-pimara-9(11)-en-4-carboxylate prepared in the above Example 51 in 1 ml of dimethylsulfoxide, was added 0.1 ml of tetrabutylammonium fluoride solution (1M). The reaction mixture was stirred at room temperature for 1 hour, diluted with 20 ml of ethyl acetate, washed with hydrochloric acid solution (0.5M) and brine, dried over magnesium sulfate, and then filtered. The filtrate was concentrated under reduced pressure to give a residue, which was purified by silica gel column chromatography (eluent: ethyl acetate/hexane=1/3) to afford 11 mg of 16-mehoxyethoxymethoxy-(−)-pimara-9(11)-en-4-carboxylic acid (91%).

$^1$H-NMR(300 MHz, CDCl$_3$): 5.28(m, 1H), 4.64(s, 2H), 3.56(m, 6H), 3.33(s, 3H), 0.76–2.20(m, 18H), 1.17(s, 3H), 0.91(s, 3H), 0.80(s, 3H),

Mass(EI) m/e 333(M$^+$-methoxyethoxy)

EXAMPLE 53

2'-(Trimethylsilyl)Ethyl 15-Formyl-(−)-Pimara-9(11)-En-4-Carboxylate 27.7 mg of 2'-(trimethylsilyl)ethyl 16-hydroxy-(−)-pimara-9(11)-en-4-carboxylate prepared in the above Example 44, catalytic amount of tetrapropylammonium perruthenate, 12.5 mg of N-methylmorpholine-N-oxide, and molecular sieve powder were dissolved in 2 ml of dichloromethane and then stirred at room temperature for 1 hour. The reaction mixture was concentrated under reduced pressure, diluted with diethyl ether, and filtered with silica gel. The filtrate was concentrated under reduced pressure to give a residue, which was purified by silica gel column chromatography (eluent: ethyl acetate/hexane=1/20) to afford 27 mg of 2'-(trimethylsilyl)ethyl 15-formyl-(−)-pimara-9 (11)-en-4-carboxylate (98%).

$^1$H-NMR(400 MHz, CDCl$_3$): 9.83(m, 1H), 5.31(m, 1H), 4.07(m, 2H) 0.71–2.40(m, 20H), 1.13(s, 3H), 0.99(s, 3H), 0.88(s, 3H), 0.00(s, 9H)

EXAMPLE 54

2'-(Trimethylsilyl)Ethyl 16-Methoxyimino-(−)-Pimara-9(11)-En-4-Carboxylate 30 mg of 2'-(trimethylsilyl)ethyl 15-formyl-(−)-pimara-9 (11)-en-4-carboxylate prepared in the above Example 53 was dissolved in 1.5 ml of pyridine. 32 mg of methoxylamine hydrochloride was added to the reaction mixture, which was then stirred at room temperature for 20 hours. The reaction mixture was concentrated under reduced pressure, diluted with diethyl ether, and filtered with silica gel. The filtrate was concentrated under reduced pressure to give a residue, which was purified by silica gel column chromatography (eluent: ethyl acetate/hexane=1/20) to afford 29 mg of 2'-(trimethylsilyl)ethyl 16-methoxyimino-(−)-pimara-9(11)-en-4-carboxylate (90%, trans:cis=2:1).

trans isomer $^1$H-NMR(400 MHz, CDCl$_3$): 7.39(t, 1H, J=6.9 Hz), 5.31(m, 1H), 4.08(m, 2H), 3.79(s, 3H), 0.75–2.25 (m, 20H), 1.13(s, 3H), 0.87(s, 3H), 0.85(s, 3H), 0.00(s, 9H)

cis isomer $^1$H-NMR(400 MHz, CDCl$_3$): 6.70(t, 1H, J=5.7 Hz), 5.31(m, 1H), 4.08(m, 2H), 3.81(s, 3H), 0.75–2.25(m, 20H), 1.13(s, 3H), 0.87(s, 3H), 0.85(s, 3H), 0.00(s, 9H)

EXAMPLE 55

16-Methoxyimino-(−)-Pimara-9(11)-En-4-Carboxylic Acid

To a solution of 29 mg of 2'-(trimethylsilyl)ethyl 16-methoxyimino-(−)-pimara-9(11)-en-4-carboxylate prepared in the above Example 54 in 1 ml of dimethylsulfoxide, was added 0.2 ml of tetrabutylammonium fluoride solution (1M). The reaction mixture was stirred at room temperature for 1 hour, diluted with 20 ml of ethyl acetate, washed with hydrochloric acid solution (0.5M) and brine, dried over magnesium sulfate, and then filtered. The filtrate was concentrated under reduced pressure to give a residue, which was purified by silica gel column chromatography (eluent: ethyl acetate/hexane=1/8) to afford 21 mg of 16-methoxyimino-(−)-pimara-9(11)-en-4-carboxylic acid (90%. trans: cis=2:1).

trans isomer $^1$H-NMR(400 MHz, CDCl$_3$): 7.36(t, 1H, J=6.9 Hz), 5.29(m, 1H), 3.76(s, 3H), 0.70–2.24(m, 18H), 1.17(s, 3H), 0.91(s, 3H), 0.83(s, 3H)

cis isomer $^1$H-NMR(400 MHz, CDCl$_3$): 6.68(t, 1H, J=5.7 Hz), 5.29(m, 1H), 3.79(s, 3H), 0.70–2.24(m, 18H), 1.17(s, 3H), 0.91(s, 3H), 0.83(s, 3H)

Mass(EI) m/e 347(M$^+$)

EXPERIMENTAL EXAMPLE 1

Inhibition Effect of Natural Single Material and Synthetic Derivatives Thereof Against PGE$_2$ Synthesis The inhibition effect of the novel derivatives against PGE2 synthesis was tested in vitro. The said inhibition effect is brought on by inhibiting cyclooxygenase-2 activity. The novel derivatives were synthesized from (−)-pimara-9(11), 15-diene-4-carboxylic acid, which is a diterpene compound isolated from root-bark of *Acanthopanax Koreanum*.

The testing process was as follows:

3 Unit of COX-2 (Layman chemical) that is separated from sheep placenta and purified was mixed with 1.0 mM of hematin, 1.95 mM of 1-epineprine and 0.49 mM of reduced glutathion, all as a cofactor. The mixture was stranded on ice for 5 min. To the mixture, the sample for assay of COX-2 activity was added, and then incubated on ice for 10 min. After preincubation, 0.02 μCi of [1-$^{14}$C] arachidonic acid, as an substrate, was added, and reacted at 37° C. for 20 min. For the termination of the reaction, 10 μl of 2 M HCl was added. Prostaglandin produced was extracted with ethyl-ether twice. Two ethylether layers were integrated, and the solvent was evaporated at a 37° C. water-bath. The concentrate was dissolved in acetone, loaded at TLC plate, and then developed with a mixed solvent of CHCl$_3$: MeOH: acetic acid (18.1.1). PGE$_2$ part of TLC plate developed was observed using autoradiography (PACKARD). The amount of PGE$_2$ decreased by the sample was compared with reference, and then COX-2 inhibition activity of the sample was determined.

The test result was showed in the following Table 1. IC$_{50}$ is the concentration of test sample that can inhibit 50% of PGE activity.

TABLE 1

Inhibition effect of natural single material and synthetic derivatives thereof against PGE$_2$ synthesis, the said inhibition effect brought on by inhibiting of COX-2 activity.

| Material | Teas Samples | | | | IC$_{50}$ (μM) |
|---|---|---|---|---|---|
| | R$_4$ | R$_1$ | R$_2$ | R$_3$ | |
| Natural Component | | | | | 790.4 |
| Aspirin | | | | | 33865.7 |
| Indomethacin | | | | | 82.0 |
| NS-398 | | | | | 38.4 |

TABLE 1-continued

Inhibition effect of natural single material and synthetic derivatives thereof against $PGE_2$ synthesis, the said inhibition effect brought on by inhibiting of COX-2 activity.

| Material | Teas Samples | | | | $IC_{50}$ ($\mu M$) |
|---|---|---|---|---|---|
| | $R_4$ | $R_1$ | $R_2$ | $R_3$ | |
| Example 1 | $CH_2OH$ | Double bond | Double bond | Vinyl | >2000 |
| Example 5 | CHCHCOOH | Double bond | Double bond | Vinyl | 82.3 |
| Example 7 | CHCHCOOH | Double bond | Double bond | Vinyl | 69.7 |
| Example 9 | $CH_2CH_2COOH$ | Double bond | Double bond | Vinyl | 105.0 |
| Example 11 | $CONH_2$ | Double bond | Double bond | Vinyl | >2000 |
| Example 12 | $CONHCH_2$ | Double bond | Double bond | Vinyl | >2000 |
| Example 13 | $CONHNH_2$ | Double bond | Double bond | Vinyl | 41.9 |
| Example 14 | CONHOH | Double bond | Double bond | Vinyl | 818.9 |
| Example 15 | $CO_2H$ | Double bond | Double bond | $CH_2CH_2OH$ | >2000 |
| Example 19 | $CO_2H$ | OH | H | $CH_2CH_2OH$ | >2000 |
| Example 21 | $CO_2H$ | Double bond | Double bond | Isoxazolinyl | >2000 |
| Example 23 | $CH_2CHCHCO_2H$ | Double bond | Double bond | Vinyl | 32.0 |
| Example 25 | $CH_2CH_2CH_2CO_2H$ | Double bond | Double bond | Vinyl | 49.4 |
| Example 29 | $CHCHCHCHCO_2H$ | Double bond | Double bond | Vinyl | 26.8 |
| Example 33 | $CH_2CH_2CHCHCO_2H$ | Double bond | Double bond | Vinyl | 63.8 |
| Example 35 | $CH_2CH_2CH_2CH_2CO_2H$ | Double bond | Double bond | Vinyl | 38.7 |
| Example 38 | $CH_2CONHSO_2PhI$ | Double bond | Double bond | Vinyl | 72.2 |
| Example 40 | $CH_2CH_2CONHSO_2PhI$ | Double bond | Double bond | Vinyl | 60.7 |
| Example 41 | $CH_2CH_2CONHSO_2Me$ | Double bond | Double bond | Vinyl | 179.8 |
| Example 43 | $CHCHCHCHCONHSO_2PhI$ | Double bond | Double bond | Vinyl | 25.6 |
| Example 46 | $CO_2H$ | Double bond | Double bond | $CH_2CH_2OMe$ | >2000 |
| Example 48 | $CO_2H$ | Double bond | Double bond | $CH_2CH_2OAc$ | 1420 |
| Example 50 | $CO_2H$ | Double bond | Double bond | $CH_2CH_2OMOM$ | >2000 |
| Example 52 | $CO_2H$ | Double bond | Double bond | $CH_2CH_2OMeM$ | >2000 |
| Example 55 | $CO_2H$ | Double bond | Double bond | $CH_2CHNOCH_3$ | >2000 |

In the above test result, the compound according to the present invention can show the 50% inhibition effect of $PGE_2$ synthesis only at 26 $\mu M$ of its concentration minimally while indomethacin, which is a conventional anti-inflammatory analgesic agent, needs the concentration of about 84 $\mu M$ for the said effect. Therefore, it is ascertained that the compound according to the present invention has the anti-inflammatory activity increased at max 3.2 times, compared to indomethacin. Compared with NS-398 [Prostaglandins Vol.47, p55(1994) and Gen. Pharmac. Vol.24, No.1 pp105–110(1993)] of Taisho Pharmaceutical Company, the compound according to the present invention showed the powerful activity 1.5 times. It is generally known that the said NS-398 has the excellent selective inhibition effect of COX-2 against COX-1.

EXPERIMENTAL EXAMPLE 2

Anti-Inflammatory Activity of Natural Single Material and Synthetic Derivatives Thereof Against Acute Inflammation For some of the natural single material and synthetic derivatives thereof, of which the inhibition effect against PGE2 synthesis was tested in Experimental example 1, the anti-inflammatory activity against arthritis was tested using a mono-arthritis model as follows:

(A) Administration of derivatives and induction of arthritis

Derivatives synthesized were dissolved in the mixed solvent of ethanol: Tween 80: saline (1:1:8), and then administered by intrapertioneal injection. Referring to the result of the in vitro test, 5 mg/kg was used as a dose for primary screening test. Adjuvant that was dissolved in mineral oil and then sterilized, was administered into tibeo-calcanean joint of right crus posterius of rat to induce arthritis. The injection volume is controlled to be contained M. butyricum 100 µg/50 µl.

(B) Determination of effect of derivatives

Edema degree was determined primarily, and the degree was used as an index of inflammation. The degree was determined by the estimation method for section area of tibeo-calcanean joint part. Width and length measurements of the joint part were taken according to time schedule upon inducing inflammation, and the width multiplied by the length. The multiplied value was then used as a section area index (SAI). On the basis of the section area index, edema index was calculated as follows:

$$\text{Edema Index (\%)} = \frac{(\text{SAI of inflammatory joint}-\text{SAI of normal joint})}{\text{SAI of normal joint}} \times 100$$

Each index was determined at 1, 4 and 24 hours after adjuvant injection. The index value determined at the same part before adjuvant injection was used as one of normal joint.

Unpaired t-test or ANOVA using Fisher PLSD verified the statistical significance.

(C) Test result of anti-inflammation

For diterpene derivatives of formula 5, 7, 8 and 18, which have excellent inhibition effect against $PGE_2$ synthesis, in vivo activity against single arthritis was tested using koprofen and indomethacin as a reference drug.

The derivatives of formula 5 and 7 showed the effect of decreasing the edema index size to be not more then half at 1 hour after inducing inflammation. That effect is more excellent than those of koprofen and indometacin. The said derivatives showed an even superior effect, also after 4 hours, then koprofen or indometacin does.

EXPERIMENTAL EXAMPLE 3

Test of Cytotoxicity of Derivatives Synthesized from Natural Single Material To investigate the utility of diterpene derivatives synthesized, cytotoxicities of some derivatives were tested.

The cytotoxicity was tested using Raw 264.7. The cytotoxicity and non-cytotoxicity were judged by performing MTT assay at 48 hours after sample treatment.

The test result was given in the following Table 2.

TABLE 2

Test of cytotoxicity of derivatives synthesized from natural single material.

| Material name | Teas Samples | | | | $IC_{50}$ (mM) |
|---|---|---|---|---|---|
| | $R_4$ | $R_1$ | $R_2$ | $R_3$ | |
| Example 5 | CHCHCOOH | double bond | double bond | Vinyl | 0.1395 |
| Example 7 | CH CHCOOH | double bond | double bond | Vinyl | 0.1390 |
| Example 9 | $CH_2\ CH_2COOH$ | double bond | double bond | Vinyl | 0.1145 |
| Example 15 | $CO_2H$ | double bond | double bond | $CH_2CH_2OH$ | 0.1390 |

TABLE 2-continued

Test of cytotoxicity of derivatives synthesized from natural single material.

| Material name | Teas Samples | | | | $IC_{50}$ (mM) |
|---|---|---|---|---|---|
| | $R_4$ | $R_1$ | $R_2$ | $R_3$ | |
| Example 16 | $CO_2H$ | $H_2$ | H | $CH_2CH_2OH$ | 0.1370 |
| Example 19 | $CO_2H$ | OH | H | $CH_2CH_2OH$ | 0.1515 |
| Example 21 | $CO_2H$ | double bond | double bond | Isoxazolinyl | 0.2500 |

In the test result of cytotoxicity, each derivative mostly showed a low cytotoxicity. Therefore, it is clear that the derivatives synthesized can be used as a medicine, that is, anti-inflammatory analgesic agent.

Pharmaceutical Preparation Example

| 1. Preparation of tablet | |
|---|---|
| Compound of Example 35 | 2.5 mg |
| Lactose BP | 151.0 mg |
| Starch BP | 30.0 mg |
| Pregelatinized corn starch BP | 15.0 mg |

Compound of Example 35 was sieved, mixed with lactose, starch and pregelatinized corn starch. To the mixture, purified water was added. The paste was granulated, dried, mixed with magnesium stearate, and then compressed to obtain tablet.

| 2. Preparation of injection (anticancer agent) | |
|---|---|
| Compound of Example 35 | 800 µg |
| d-HCl | to be pH 3.5 |
| Saline for Injection BP | maximum 1 ml |

Compound of Example 35 was dissolved in proper volume of saline for injection BP. The pH of the resultant solution was controlled with d-HCl BP to be pH 3.5, and then its volume was controlled with saline for Injection BP. The solution mixed completely was filled in 5-ml type 1 ample maken of glass. The top of ample was fused for sealing. The solution contained in ample was autoclaved at 120° C. for 15 min to be sterilized and to obtain an injection.

Industrial Applicability

The present invention confirmed the fact that the effect of inhibiting $PGE_2$ synthesis in vitro of novel derivatives of the present invention, which are synthesized according to the process of the present invention from (−)-pimara-9(11),15-diene-4-carboxylic acid of Chemical Formula 2, a diterpene compound isolated from root-bark and bark of Acanthopanax Koreanum, is superior to indomethacin, and these compounds have 3.2-fold physiological activity of anti-inflammatory action. These compounds also showed excellent effect in anti-inflammatory experiments using animal models with low toxicity. Thus, the diterpene component of Acanthopanax Koreanum and synthetic derivatives thereof can be usefully employed as an anti-inflammatory analgesic agent.

What is claimed is:

1. A diterpene derivative represented by Chemical Formula 1:

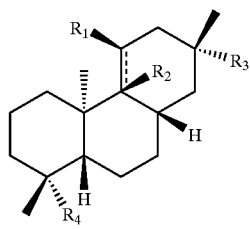

(chemical formula 1)

wherein $R_1$ and $R_2$ individually represent hydrogen or hydroxy, or they form a double bond in the cycle; $R_3$ represents a vinyl, hydroxyethyl, methoxyethyl, acetyloxyethyl, methoxymethoxyethyl, methoxyethoxymethoxyethyl, methoxyiminoethyl or isoxazolinyl group; and $R_4$ represents a hydroxymethyl, carboxyl, carboxymethyl, carboxyvinyl, carboxyethyl, carboxypropyl, carboxybutyl, carboxybutadienyl, carboxyallyl, carboxyhomoallyl, carbamoyl, methylcarbamoyl, hydroxycarbamoyl, carbazoyl, N-pipsylcarbamoylmethyl, N-pipsylcarbamoylethyl, N-pipsylcarbamoylbutadienyl or N-methanesulfonylcarbamoylethyl group, with the proviso that when $R_1$ and $R_2$ form a double bond in the cycle and $R_3$ is vinyl, $R_4$ is not carboxyl.

2. A diterpene derivative according to claim 1, wherein $R_1$ and $R_2$ form a double bond in the cycle, $R_3$ represents vinyl, and $R_4$ represents a hydroxymethyl, carboxymethyl, carboxyvinyl, carboxyethyl, carboxypropyl, carboxybutyl, carboxybutadienyl, carboxyallyl, carboxyhomoallyl, carbazoyl, N-pipsylcarbamoylmethyl, N-pipsylcarbamoylethyl, N-pipsylcarbamoylbutadienyl or N-methanesulfonylcarbamoylethyl group.

3. An anti-inflammatory analgesic agent comprising the diterpene derivative of claim 1 as an active ingredient.

4. An anti-inflammatory analgesic agent according to claim 3, wherein the anti-inflammatory analgesic agent is in the form of a tablet.

5. An anti-inflammatory analgesic agent according to claim 3, wherein the anti-inflammatory analgesic agent is in the form of an injectable formulation.

6. A method for treating inflammation, wherein the method comprises administering an effective amount of a diterpene derivative represented by Chemical Formula 1:

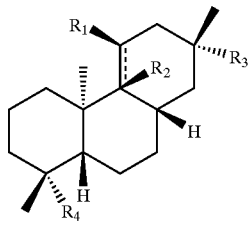

(chemical formula 1)

wherein $R_1$ and $R_2$ individually represent hydrogen or hydroxy, or they form a double bond in the cycle; $R_3$ represents a vinyl, hydroxyethyl, methoxyethyl, acetyloxyethyl, methoxymethoxyethyl, methoxyethoxymethoxyethyl, methoxyiminoethyl or isoxazolinyl group; and $R_4$ represents a carboxyl, carboxymethyl, carboxyvinyl, carboxyethyl, carboxypropyl, carboxybutyl, carboxybutadienyl, carboxyallyl, carboxyhomoallyl, carbamoyl, methylcarbamoyl, hydroxycarbamoyl, carbazoyl, N-pipsylcarbamoylmethyl, N-pipsylcarbamoylethyl, N-pipsylcarbamoylbutadienyl or N-methanesulfonylcarbamoylethyl group, with the proviso that when $R_1$ and $R_2$ form a double bond in the cycle and $R_3$ is vinyl, $R_4$ is not carboxyl.

7. A pharmaceutical composition comprising the diterpene derivative of claim 1.

* * * * *

UNITED STATES PATENT AND TRADEMARK OFFICE
CERTIFICATE OF CORRECTION

PATENT NO. : 6,593,363 B1
DATED : July 15, 2003
INVENTOR(S) : Young Ger Suh et al.

It is certified that error appears in the above-identified patent and that said Letters Patent is hereby corrected as shown below:

Column 37,
Lines 22 and 34, delete "hydroxymethyl,".

Column 38,
Lines 1-3, delete the claim in its entirety and insert therefor:
An anti-inflammatory analgesic agent comprising a diterpene derivative represented by Chemical Formula 1:

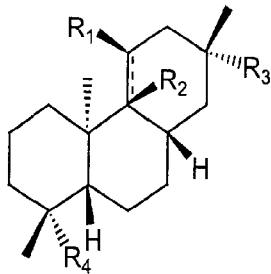

(chemical formula 1)

wherein $R_1$ and $R_2$ individually represent hydrogen or hydroxy, or they form a double bond in the cycle; $R_3$ represents a vinyl, hydroxyethyl, methoxyethyl, acetyloxyethyl, methoxymethoxyethyl, methoxyethoxymethoxyethyl, methoxyiminoethyl or isoxazolinyl group; and $R_4$ represents a hydroxymethyl, carboxyl, carboxymethyl, carboxyvinyl, carboxyethyl, carboxypropyl, carboxybutyl, carboxybutadienyl, carboxyallyl, carboxyhomoallyl, carbamoyl, methylcarbamoyl, hydroxycarbamoyl, carbazoyl, N-pipsylcarbamoylmethyl, N-pipsylcarbamoylethyl, N-pipsylcarbamoylbutadienyl or N-methanesulfonylcarbamoylethyl group, with the proviso that when $R_1$ and $R_2$ form a double bond in the cycle and $R_3$ is vinyl, $R_4$ is not carboxyl,     wherein the anti-inflammatory analgesic agent is in the form of a tablet.

UNITED STATES PATENT AND TRADEMARK OFFICE
CERTIFICATE OF CORRECTION

PATENT NO.    : 6,593,363 B1
DATED         : July 15, 2003
INVENTOR(S)   : Young Ger Suh et al.

It is certified that error appears in the above-identified patent and that said Letters Patent is hereby corrected as shown below:

Column 38 cont'd,
Lines 4-6, delete the claim in its entirety and insert therefor:
An anit-inflammatory analgesic agent comprising a diterpene derivative represented by Chemical Formula 1:

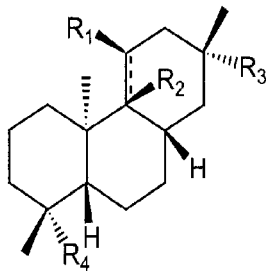

(chemical formula 1)

wherein $R_1$ and $R_2$ individually represent hydrogen or hydroxy, or they form a double bond in the cycle; $R_3$ represents a vinyl, hydroxyethyl, methoxyethyl, acetyloxyethyl, methoxymethoxyethyl, methoxyethoxymethoxyethyl, methoxyiminoethyl or isoxazolinyl group; and $R_4$ represents a hydroxymethyl, carboxyl, carboxymethyl, carboxyvinyl, carboxyethyl, carboxypropyl, carboxybutyl, carboxybutadienyl, carboxyallyl, carboxyhomoallyl, carbamoyl, methylcarbamoyl, hydroxycarbamoyl, carbazoyl, N-pipsylcarbamoylmethyl, N-pipsylcarbamoylethyl, N-pipsylcarbamoylbutadienyl or N-methanesulfonylcarbamoylethyl group, with the proviso that when $R_1$ and $R_2$ form a double bond in the cycle and $R_3$ is vinyl, $R_4$ is not carboxyl,     wherein the anti-inflammatory analgesic agent is in the form of an injectable formulation.

Signed and Sealed this

Eleventh Day of November, 2003

JAMES E. ROGAN
*Director of the United States Patent and Trademark Office*